United States Patent
Tino

[11] Patent Number: 5,965,577
[45] Date of Patent: Oct. 12, 1999

[54] HETEROCYCLIC INHIBITORS OF MICROSOMAL TRIGLYCERIDE TRANSFER PROTEIN AND METHOD

[75] Inventor: Joseph A. Tino, Lawrenceville, N.J.

[73] Assignee: Bristol-Myers Squibb Company, Princeton, N.J.

[21] Appl. No.: 08/986,854

[22] Filed: Dec. 8, 1997

Related U.S. Application Data

[60] Provisional application No. 60/033,899, Dec. 20, 1996.
[51] Int. Cl.[6] .................... A61K 31/445; A61K 31/47; A61K 31/495; C07D 211/58; C07D 233/78; C07D 401/12; C07D 471/10
[52] U.S. Cl. .................... 514/325; 514/236.8; 514/256; 514/318; 514/319; 514/320; 514/321; 514/322; 514/324; 514/326; 514/331; 514/397; 514/422; 514/429; 514/325; 544/88; 544/130; 544/287; 544/360; 544/405; 546/200; 546/202; 546/203; 546/208; 546/22; 546/189; 546/193; 546/198; 548/119; 548/312.1; 548/338.1
[58] Field of Search .................... 546/200, 201, 546/202, 203, 208, 198, 193, 189, 22; 514/325, 324, 321, 318, 316, 289, 235.5, 255, 228.8, 323, 252; 544/88, 130, 287, 360, 405; 548/119, 312.1, 338.1

[56] References Cited

U.S. PATENT DOCUMENTS

| | | | |
|---|---|---|---|
| 3,754,001 | 8/1973 | Timmer et al. | 548/255 |
| 5,712,279 | 1/1998 | Biller et al. | 514/252 |
| 5,780,465 | 7/1998 | Markley et al. | 514/224.7 |

FOREIGN PATENT DOCUMENTS

| | | |
|---|---|---|
| 0643057A1 | 3/1995 | European Pat. Off. . |
| WO96/26205 | 8/1996 | WIPO . |
| WO97/26240 | 7/1997 | WIPO . |
| WO27/43257 | 11/1997 | WIPO . |

OTHER PUBLICATIONS

U.S. Application No. 08/842,132 filed Apr. 23, 1997.
U.S. Application No. 08/847,775, filed Apr. 23, 1997.

*Primary Examiner*—Ceila Chang
*Attorney, Agent, or Firm*—Burton Rodney

[57] ABSTRACT

Novel compounds are provided which are inhibitors of MTP and thus are useful for lowering serum lipids and treating atherosclerosis and related diseases, and have the structure

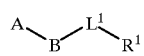

including pharmaceutically acceptable salts thereof, or prodrug esters thereof, A is

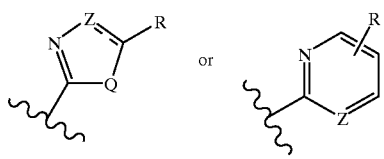

where Z is N or CH, or where Z is

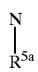

or $CH_2$ when --- is a single bond;

Q is (1) —O—;
(2) —S—; or (3) 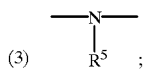 ;

B is:

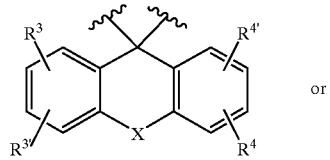

or

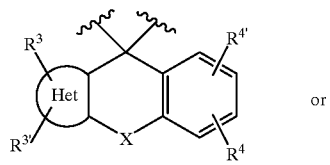

or

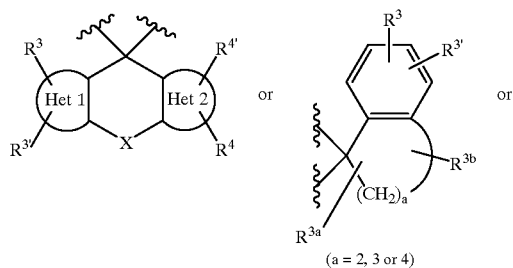

(a = 2, 3 or 4)

-continued
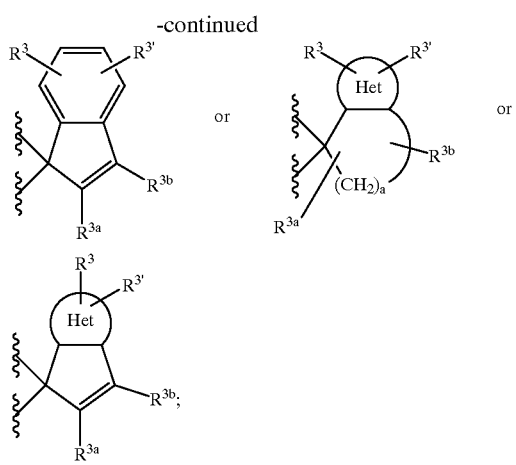
and wherein $L^1$, R, $R^1$, $R^3$, $R^{3'}$, $R^{3a}$, $R^{3b}$, $R^4$, $R^{4'}$, $R^5$, $R^{5a}$, X,
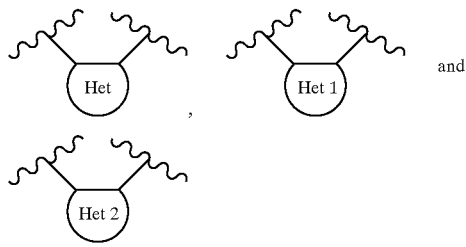
are as defined herein.
12 Claims, No Drawings

HETEROCYCLIC INHIBITORS OF MICROSOMAL TRIGLYCERIDE TRANSFER PROTEIN AND METHOD

This application is based on U.S. Provisional Application 60/033,899 filed Dec. 20, 1996.

FIELD OF THE INVENTION

This invention relates to novel heterocyclic compounds which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, Chem. Phys. Lipids 38, 205—22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, Chem. Phys. Lipids 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., J. Biol. Chem. 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, Nature 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., J. Biol. Chem. 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., Biochemistry 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, Biochem. Biophys. Acta 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in The Metabolic Basis of Inherited Disease, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., Clin. Chem. 34, B9–12 (1988). A link between the apoB gene and abetalipoproteinemia has been excluded in several families. Talmud et al., J. Clin. Invest. 82, 1803–6 (1988) and Huang et al., Am. J. Hum. Genet. 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, Biochem. Biophys. Acta 857, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., J. Biol. Chem. 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, J. Cell Biol. 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event. However, there is no direct evidence in the prior art demonstrating that MTP plays a role in lipid metabolism or the assembly of plasma lipoprotein.

Recent reports (Science, Vol. 258, page 999, 1992; D. Sharp et al, Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)) which is incorporated herein by reference), reports MTP inhibitors which also block the production of apoB containing lipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

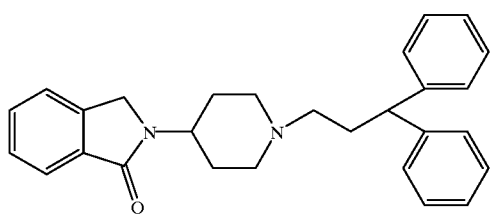

which has the name 2-[1-(3,3-diphenylpropyl)-4-piperidinyl]-2,3-dihydro-3-oxo-1H-isoindole hydrochloride and

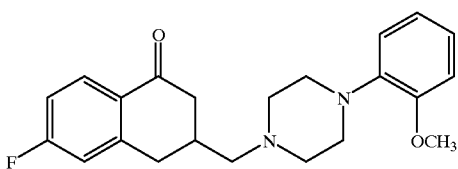

which has the name 1-[3-(6-fluoro-1-tetralanyl)-methyl]-4-O-methoxyphenyl piperazine.

EP 0643057A1 published Mar. 15, 1995, discloses MTP inhibitors of the structure

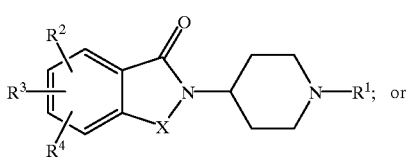

I

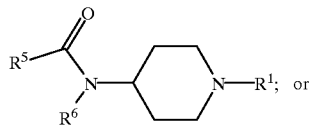

II

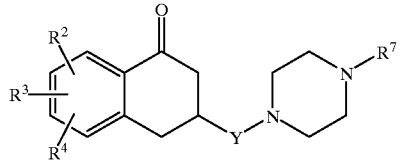

III where X is: $CHR^8$,

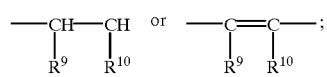

or 

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is $-(CH_2)_m-$ or

where m is 2 or 3;

$R^1$ is alkyl, alkenyl, alkynyl, aryl, heteroaryl, arylalkyl (wherein alkyl has at least 2 carbons), diarylalkyl, arylalkenyl, diarylalkenyl, arylalkynyl, diarylalkynyl, diarylalkylaryl, heteroarylalkyl (wherein alkyl has at least 2 carbons), cycloalkyl, or cycloalkylalkyl (wherein alkyl has at least 2 carbons); all of the aforementioned $R^1$ groups being optionally substituted through available carbon atoms with 1, 2, or 3 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a group of the structure

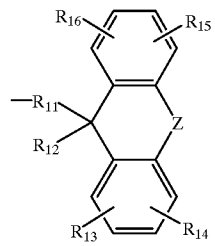

$R^{11}$ is a bond, alkylene, alkenylene or alkynylene of up to 6 carbon atoms, arylene (for example

), or mixed arylene-alkylene (for example

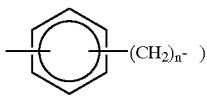

where n is 1 to 6;

$R^{12}$ is hydrogen, alkyl, alkenyl, aryl, heteroaryl, haloalkyl, arylalkyl, arylalkenyl, cycloalkyl, aryloxy, alkoxy, arylalkoxy, heteroarylalkyl or cycloalkylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, carboxy, aminocarbonyl, alkylcarbonyloxy, alkylcarbonylamino, arylalkyl, heteroaryl, heteroarylalkyl, or aryloxy;

or $R^1$ is

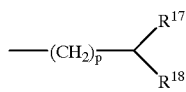

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

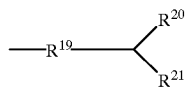

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkalkoxy;

$R^2$, $R^3$, $R^4$ are independently hydrogen, halo, alkyl, haloalkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl of at least 2 carbons, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloalkenylalkyl, polycycloalkenyl, polycycloalkenylalkyl, heteroarylcarbonyl, all of the $R^5$ and $R^6$ substituents being optionally substituted through available carbon atoms with 1, 2, or 3 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, or aryl or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino; with the proviso that when $R^5$ is $CH_3$, $R^6$ is not H; and where $R^5$ is phenyl, the phenyl preferably includes an ortho hydrophobic substituent such as alkyl, haloalkyl, aryl, aryloxy or arylalkyl;

$R^6$ is hydrogen or $C_1-C_4$ alkyl or $C_1-C_4$ alkenyl;

$R^7$ is alkyl, aryl or arylalkyl wherein alkyl or the alkyl portion is optionally substituted with oxo; and including pharmaceutically acceptable salts and anions thereof.

In the formula I compounds, where X is $CH_2$ and $R^2$ $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-O-methoxyphenyl.

U.S. application Ser. No. 472,067, filed Jun. 6, 1995 (file DC21e) discloses compounds of the structure

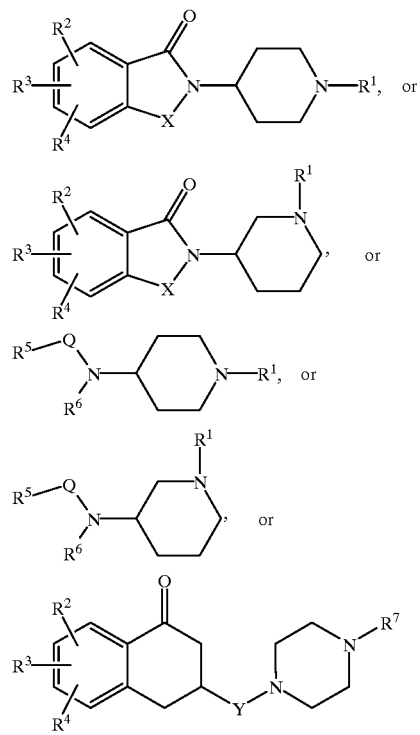

where Q is

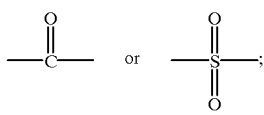

X is: CHR$^8$,

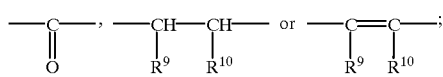

R$^8$, R$^9$ and R$^{10}$ are independently hydrogen, alkyl, alkenyl, alkynyl, aryl, arylalkyl, heteroaryl, heteroarylalkyl, cycloalkyl, or cycloalkylalkyl;

Y is —(CH$_2$)$_m$— or

wherein m is 2 or 3;

R$^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo;

or R$^1$ is a fluorenyl-type group of the structure

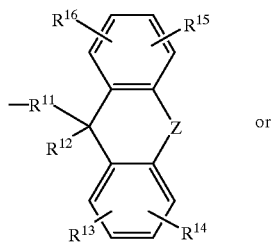

A

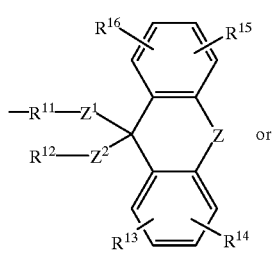

B

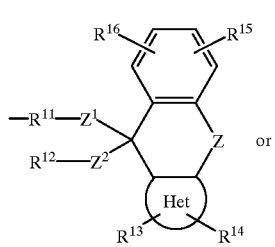

C

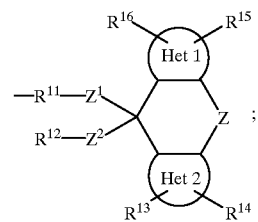

D or
R$^1$ is an indenyl-type group of the structure

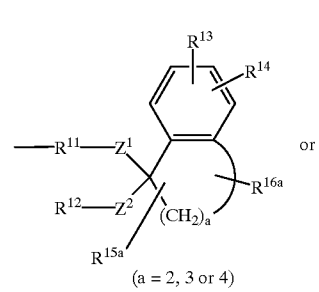

E (a = 2, 3 or 4)

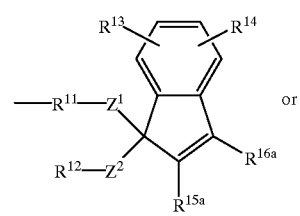

F

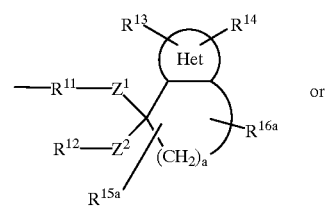

G

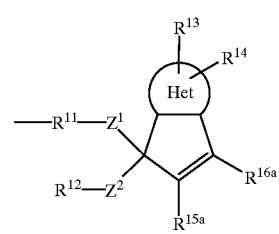

H

Z$^1$ and Z$^2$ are the same or different and are independently a bond, O, S,

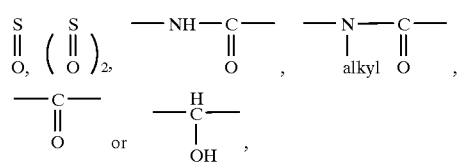

with the proviso that with respect to B, at least one of Z$^1$ and Z$^2$ will be other than a bond; R$^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that
(1) when $R^{12}$ is H, aryloxy, alkoxy or arylalkoxy, then $Z^2$ is

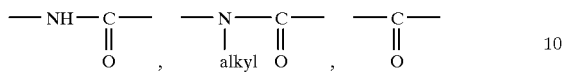

or a bond and
(2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;
or $R^1$ is a group of the structure

wherein $R^{19}$ is aryl or heteroaryl;
$R^{20}$ is aryl or heteroaryl;
$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;
$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;
$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

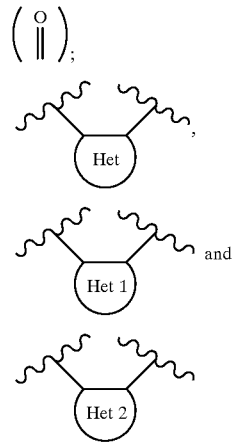

are the same or different and are independently selected from heteroaryl containing 5- or 6-ring members; and N-oxides

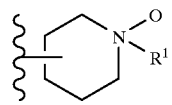

thereof; and
pharmaceutically acceptable salts thereof; with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

U.S. application Ser. No. 548,811, filed Jan. 11, 1996 (file DC21h), discloses compounds having the structure

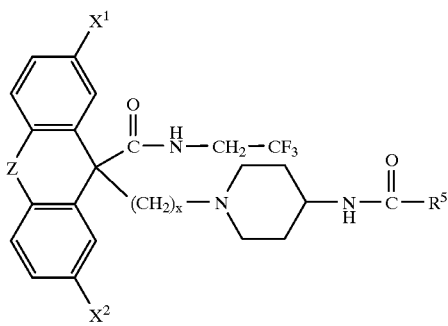

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

U.S. Provisional Application Ser. No. 60/017,253, filed May 10, 1996 (file HX82*) discloses compounds which are inhibitors of MTP and have the structure

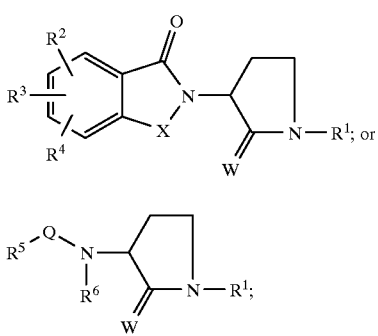

where W is H, H or O; and X, Q, $R^1$, $R^2$, $R^3$, $R^4$, $R^5$ and $R^6$ are essentially as defined in U.S. application Ser. No. 10 472,067 (file DC21e).

U.S. Provisional Application Ser. No. 60/017,254, filed May 10, 1996 (file HX84*) discloses compounds which are inhibitors of MTP and have the structure

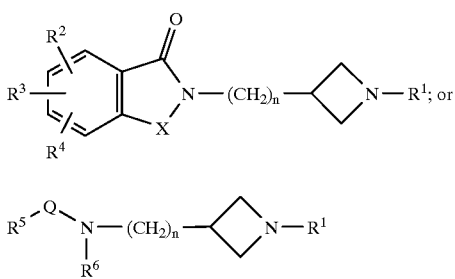

where n is 0 or 1 and X, Q, $R^1$, $R^2$, $R^3$, $R^4$, $R^5$ and $R^6$ are essentially as defined in U.S. application Ser. No. 20 472, 067 (file DC21e).

U.S. Provisional Application Ser. No. 60/017,224 (file HX79a*) filed May 7, 1996, discloses compounds which are inhibitors of MTP and have the structure

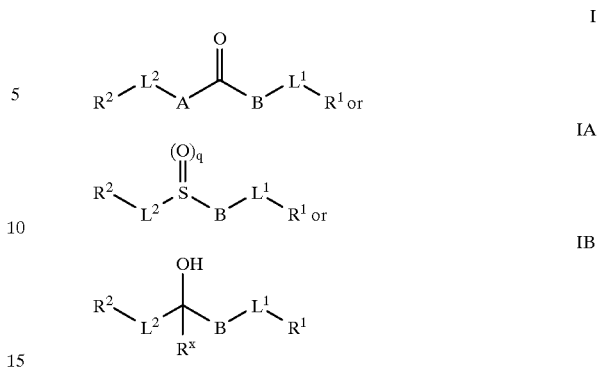

including pharmaceutically acceptable salts thereof, wherein q is 0, 1 or 2;

A is (1) a bond;
(2) —O—; or
(3)

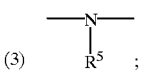

where $R^5$ is H or lower alkyl or $R^5$ together with $R^2$ forms a carbocyclic or heterocyclic ring system containing 4 to 8 members in the ring.

B is a fluorenyl-type group of the structure:

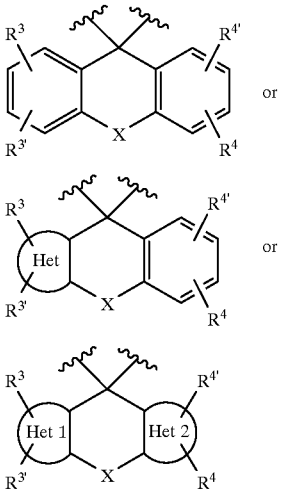

B is an indenyl-type group of the structure

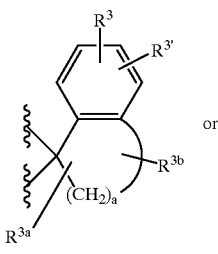

(a = 2, 3 or 4)

-continued

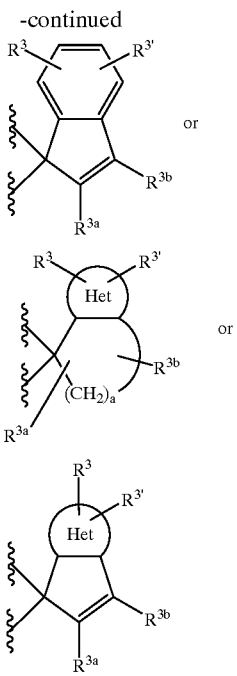

R$^x$ is H, alkyl or aryl;

R$^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO(R$^{13}$)(R$^{14}$), (where R$^{13}$ and R$^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); R$^1$ can also be aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to L$^1$ (or L$^2$ in the case of R$^2$) at the 2-position); 1,3-dioxane or 1,3-dioxolane connected to L$^1$ (or L$^2$ in the case of R$^2$) at the 4-position.

The R$^1$ group may have from one to four substituents, which can be any of the R$^3$ groups or R$^1$ groups, and certain preferred R$^1$ substituents as disclosed.

R$^2$ is the same or different from R$^1$ and is independently any of the groups set out for R$^1$, H, polyhaloalkyl (such as CF$_3$CH$_2$, CF$_3$CF$_2$CH$_2$ or CF$_3$) or cycloheteroalkyl, and may be substituted with one to four of any of the groups defined for R$^3$, or any of the substituents preferred for R$^1$.

L$^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

L$^2$ may be the same or different from L$^1$ and may independently be any of the L$^1$ groups set out above or a singe bond.

R$^3$, R$^{3\prime}$, R$^4$ and R$^{4\prime}$ may be the same or different and are independently selected from H, halogen, CF$_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R$^{3a}$ and R$^{3b}$ are the same or different and are independently any of the R$^3$ groups except hydroxy, nitro, amino or thio;

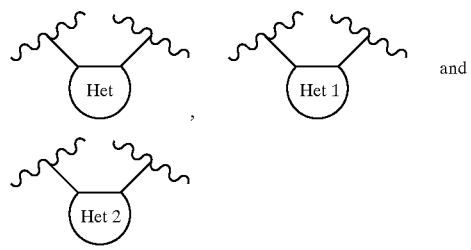

and

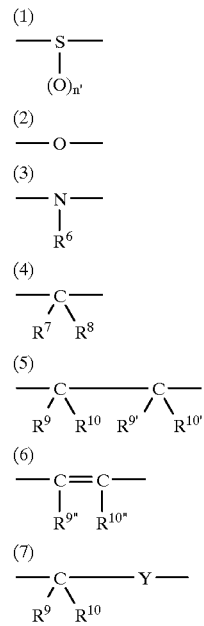

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

(1)
$$-\underset{(O)_{n'}}{\overset{|}{S}}-$$

(2)
$$-O-$$

(3)
$$-\underset{R^6}{\overset{|}{N}}-$$

(4)
$$-\underset{R^7\ R^8}{\overset{\diagup\diagdown}{C}}-$$

(5)
$$-\underset{R^9\ R^{10}}{\overset{\diagup\diagdown}{C}}-\underset{R^{9\prime}\ R^{10\prime}}{\overset{\diagup\diagdown}{C}}-$$

(6)
$$-\underset{R^{9\prime\prime}\ R^{10\prime\prime}}{\overset{|\ \ \ |}{C=C}}-$$

(7)
$$-\underset{R^9\ R^{10}}{\overset{\diagup\diagdown}{C}}-Y-$$

wherein
Y is O, N—R$^6$ or S;
n' is 0, 1 or 2;
R$^6$ is H, lower alkyl, aryl, —C(O)—R$^{11}$ or —C(O)—O—R$^{11}$;

$R^7$ and $R^8$ are the same or different and are independently H, alkyl, aryl, halogen, —O—$R^{12}$, or $R^7$ and $R^8$ together can be oxygen to form a ketone;

$R^9$, $R^{10}$, $R^{9'}$ and $R^{10'}$ are the same or different and are independently H, lower alkyl, aryl or —O—$R^{11}$;

$R^{9''}$ and $R^{10''}$ are the same or different and are independently H, lower alkyl, aryl, halogen or —O—$R^{11}$;

$R^{11}$ is alky or aryl;

$R^{12}$ is H, alkyl or aryl.

The following provisos apply to formula I compounds:

(a) when $R^1$ is unsubstituted alkyl or unsubstituted arylalkyl, $L^1$ cannot contain amino;

(b) when $R^1$ is alkyl, $L^1$ cannot contain amino and oxo in adjacent positions (to form an amido group);

(c) when $R^2L^2A$— is $H_2N$—, $R^1L^1$ cannot contain amino;

(d) when $R^1$ is cyano, $L^1$ must have more than 2 carbons;

(e) $R^1L^1$ must contain at least 3 carbons.

With respect to compounds of the invention IA and IB, $R^2L^2$ cannot have an O or N atom directly attached to S=$(O)_q$ or $CR^x(OH)$, and for IA, $R^2L^2$ cannot be H.

With respect to compounds of the invention I, IA and IB, where $R^1$ is cycloheteroalkyl, $R^1$ is exclusive of 1-piperidinyl, 1-pyrrolidinyl, 1-azetidinyl or 1-(2-oxo-pyrrolidinyl).

SUMMARY OF THE INVENTION

In accordance with the present invention, novel compounds are provided which are inhibitors of MTP and have the structure $$A_{\diagdown B}\diagdown^{L^1}\diagdown_{R^1} \qquad I$$

including pharmaceutically acceptable salts thereof, wherein A is

[structures of oxazole/thiazole-type ring with R, Z, Q and pyridine-type ring with R, Z]

where Z is N or CH, or where Z is $$\underset{R^{5a}}{\overset{\mid}{N}}$$

or $CH_2$ when --- is a single bond;

Q is (1) —O—;
(2) —S—; or
(3)

$$(3) \quad \underset{R^5}{\overset{\mid}{-N-}} \; ;$$

where $R^5$ and $R^{5a}$ are the same or different and are H, lower alkyl, aryl, heteroaryl or cycloalkyl;

R is H, alkyl, alkoxy, alkenyl, alkynyl, aryl, halo, heteroaryl, cycloheteroalkyl, heteroarylalkyl, cycloalkyl or cycloalkenyl, with the proviso that R cannot be alkoxy or halo when --- is a single bond;

B is a fluorenyl-type group of the structure:

[three fluorenyl-type structures with R³, R³', R⁴, R⁴', X, Het, Het 1, Het 2]

B is an indenyl-type group of the structure

[four indenyl-type structures with R³, R³', R³ᵃ, R³ᵇ, (CH₂)ₐ, Het]

(a = 2, 3 or 4)

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, hydroxy, amino, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, cycloheteroalkyl, cycloheteroalkylalkyl, —PO($R^{13}$)($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); $R^1$ can also be carbonylamino or aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to $L^1$ at the 2, 4, 5, or 6 position).

The $R^1$ group may have from one to four substituents, which can be any of the $R^3$ groups or $R^1$ groups, and any of the preferred $R^1$ substituents set out below.

$R^1$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

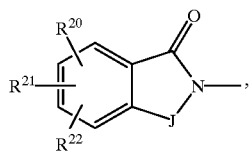

where J is: $CHR^{23}$,

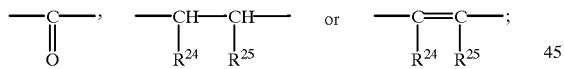

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to $R^1$, or attached via an alkylene chain at an open position.

$L^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

$R^3$, $R^{3'}$, $R^4$ and $R^{4'}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups;

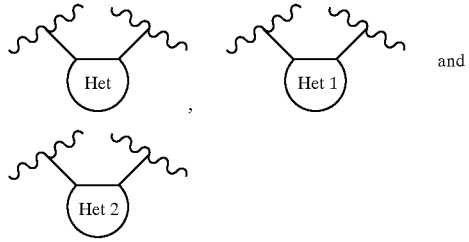

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

(1)

(2)

(3)

(4)

(5)
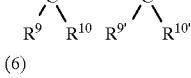

(6)
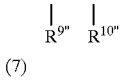

(7)
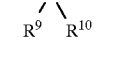

wherein
Y is O, N—$R^6$ or S;
n is 0, 1 or 2;
$R^6$ is H, lower alkyl, aryl, —C(O)—$R^{11}$ or —C(O)—O—$R^{11}$;
$R^7$ and $R^8$ are the same or different and are independently H, alkyl, aryl, halogen, —O—$R^{12}$, or $R^7$ and $R^8$ together can be oxygen to form a ketone;

$R^9$, $R^{10}$, $R^{9\prime}$ and $R^{10\prime}$ are the same or different and are independently H, lower alkyl, aryl or -O-Rll;

$R^{9\prime\prime}$ and $R^{10\prime\prime}$ are the same or different and are independently H, lower alkyl, aryl, halogen or —O—$R^{11}$;

$R^{11}$ is alky or aryl;

$R^{12}$ is H, alkyl or aryl.

Thus, the compounds I of the invention include compounds of the structure

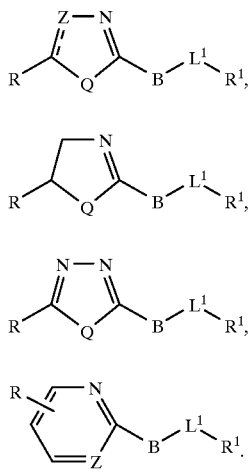

The pharmaceutically acceptable salts of the compounds of formulae I, IA, IB, IC, ID and IE include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for preventing, inhibiting or treating atherosclerosis, pancreatitis or obesity is provided, wherein a compound of formula I, IA, IB, IC, ID and IE as defined hereinbefore is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipid-emia, hyperlipoproteinemia, hypercholesterolemia, hypertriglyceridemia, hyperglycemia and/or non-insulin dependent diabetes (Type II diabetes), wherein a compound of formula I, IA or IB as defined hereinbefore (and including compounds excluded by provisos (a), (b), (c), (d) and (e) set out hereinbefore) is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e. g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., *Nature* 327, 632–634 (1987)] which may have similar catalytic properties.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents which may be any of the $R^3$ groups, or the $R^1$ substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl and cyclododecyl, cyclohexenyl,

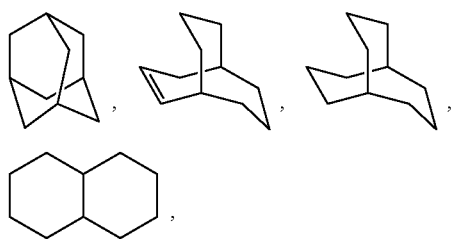

any of which groups may be optionally substituted with 1 to 4 substituents which may be any of the $R^3$ groups, or the $R^1$ substituents set out herein.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclooctanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycycloalkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl or any of the $R^3$ groups, or the $R^1$ substituents set out herein.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", "alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the $R^3$ groups, or the $R^1$ substituents set out herein.

Unless otherwise indicated, the term "lower alkynyl" or "alkynyl" as used herein by itself or as part of another group refers to straight or branched chain radicals of 2 to carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the $R^3$ groups, or the $R^1$ substituents set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Suitable alkylene, alkenylene or alkynylene groups or $(CH_2)_m$, $(CH_2)_n$ or $(CH_2)_p$ (which may include alkylene, alkenylene or alkynylene groups) as defined herein, may optionally include 1, 2, or 3 substituents which include any of the $R^3$ groups, or the $R^1$ substituents set out herein.

Examples of alkylene, alkenylene and alkynylene include

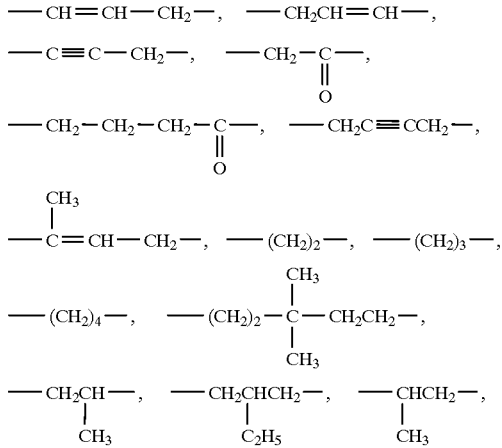

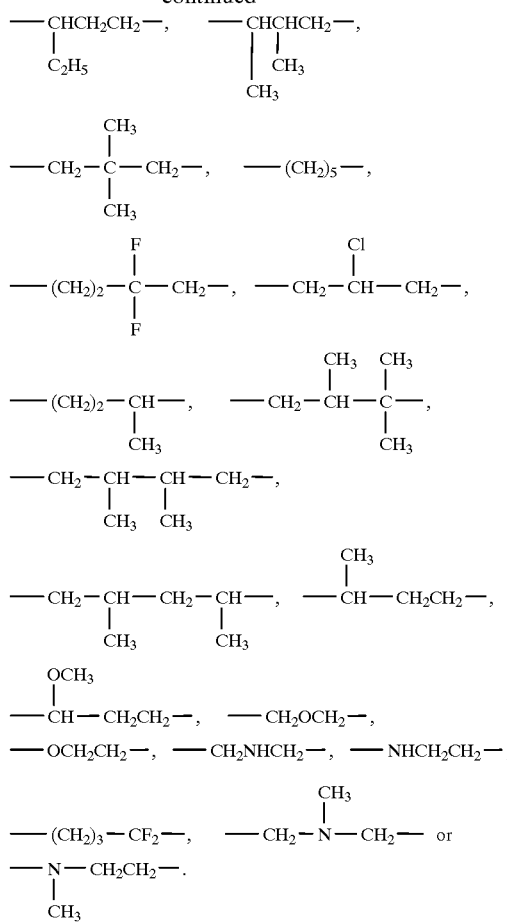

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 4-, 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

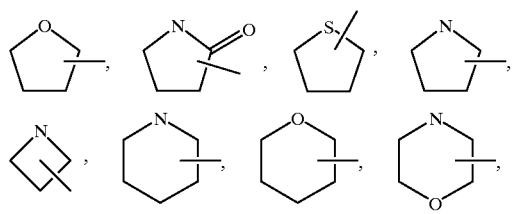

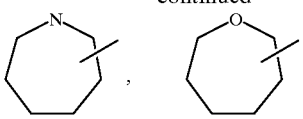

and the like. The above groups may include 1 to 4 substituents such as alkyl, halo, oxo and/or any of of the $R^3$ groups, or the $R^1$ substituents set out herein. In addition, any of the above rings can be fused to a cycloalkyl, aryl, heteroaryl or cycloheteroalkyl ring.

The term "cycloheteroalkoxy" as used herein alone or as part of another group refers to a 4-, 5-, 6- or 7-membered saturated or partially saturated ring which includes at least one oxygen atom in the ring and at least 1 or 2 other hetero atoms in the ring such as nitrogen, oxygen and/or sulfur, linked through a carbon or heteroatom, where possible, optionally via the linker $(CH_2)_p$, and which may include 1 to 4 substituents such as alkyl, halo, oxo and/or any of of the $R^3$ groups, or the $R^1$ substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides, such as

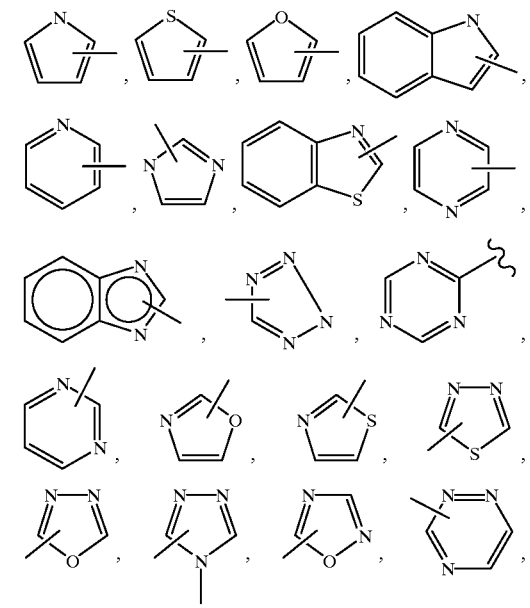

and the like.

Ar may be either aryl or heteroaryl as defined above.

-continued

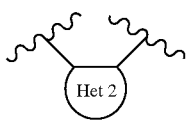

are the same or different, as defined hereinbefore, and are attached to the central ring of the indenyl or fluorenyl type group at adjacent positions (that is, ortho or 1,2-positions). Examples of such groups include

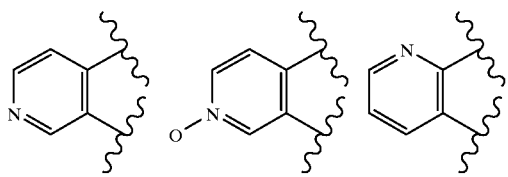
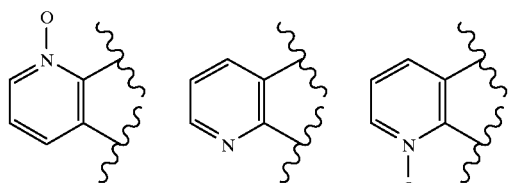
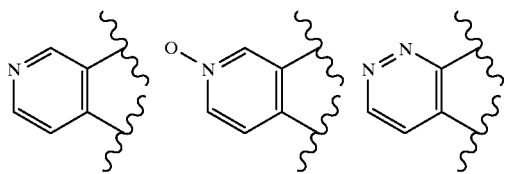
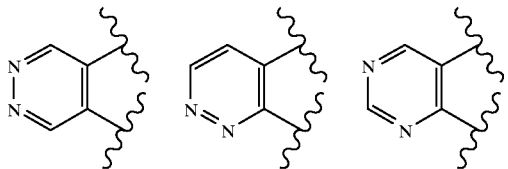
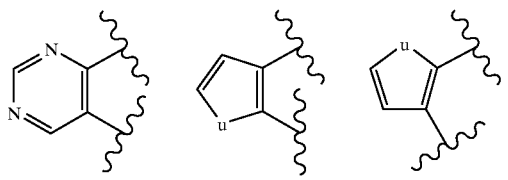
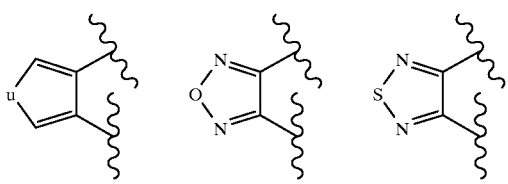
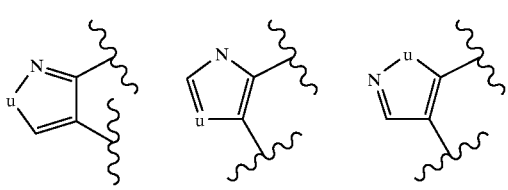

-continued

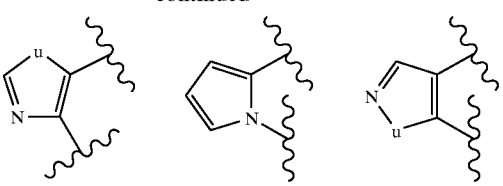

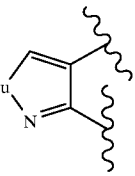

wherein u is selected from O, S, and $NR^{7a}$; $R^{7a}$ is H, lower alkyl, aryl, $—C(O)R^{7b}$, $—C(O)OR^{7b}$; $R^{7b}$ is alkyl or aryl.

The heteroaryl groups including the above groups may optionally include 1 to 4 substituents such as any of the $R^3$ groups, or the $R^1$ substituents set out herein. In addition, any of the above rings can be fused to a cycloalkyl, aryl, heteroaryl or cycloheteroalkyl ring.

The compounds I of the invention may be prepared according to the following reaction schemes.

Reaction Scheme 1A

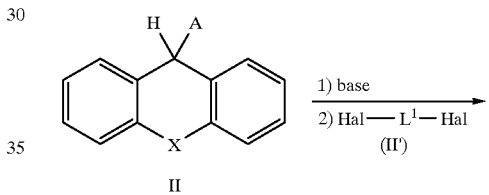

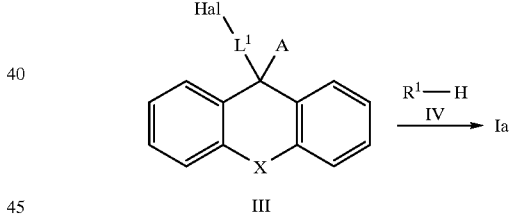

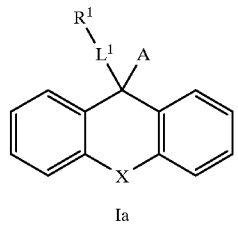

Reaction Scheme 1B

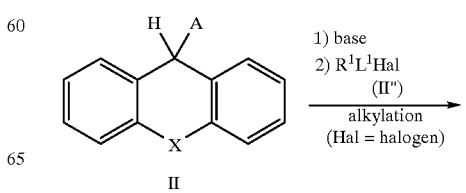

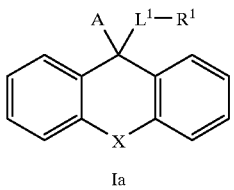

Ia

It will be appreciated that in the above reactions and the reactions to follow, unless otherwise indicated, the moiety "B" in the starting materials, intermediates and final products is set out as

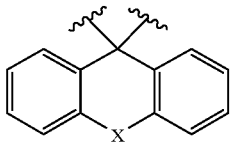

for purposes of illustration only.

It will be appreciated that the "B" moiety in the starting materials, intermediates and final products in all reactions set forth herein, unless indicated to the contrary may be any of the fluorenyl-type groups

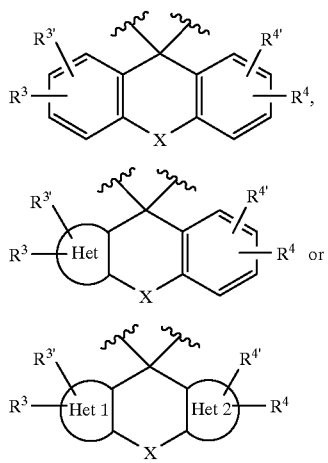

as well as any of indenyl-type groups

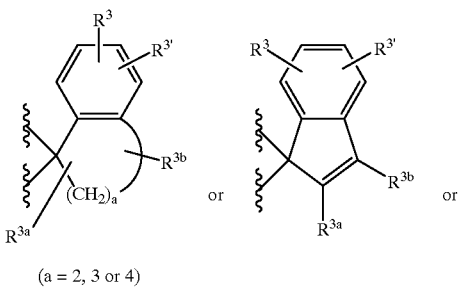

(a = 2, 3 or 4)

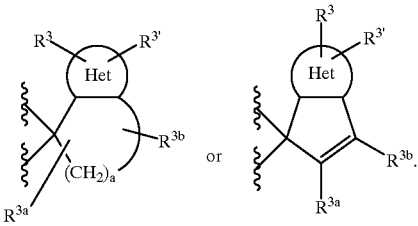

The above B moieties (including all fluorenyl-type groups and all indenyl-type groups) are collectively referred to as "fluorenyl-type" moieties. The use of the first fluorenyl-type group (as set out in the previous paragraph) in the Reaction Schemes is for purposes of illustration only; any of the 3 fluorenyl groups or 4 indenyl groups as set out above may be employed in any of the Reaction Schemes set out herein in place of

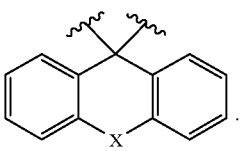

As seen in Scheme 1A, in accordance with another aspect of the present invention, the solution of compound II in an inert organic solvent, such as tetrahydrofuran, dioxane or diethyl ether, at a reduced temperature of within the range of from about −40° C. to about room temperature under an inert atmosphere such as argon, is treated with base such as potassium hydroxide, potassium tert-butoxide, lithium or potassium bis(trimethylsilylamide), or n-butyllithium in an inert organic solvent such as hexane, tetrahydrofuran or diethyl ether, while maintaining temperature of the reaction mixture below from about −40° C. to about room temperature. The reaction mixture is treated with dihalide II', for example, 1,4-diiodobutane or 1,4-dibromo-2-butene, to form the halogenated compound III.

The halogenated compound III is treated with $R^1H$ (IV) (containing an activated proton) optionally in the presence of alkali metal base such as potassium carbonate, sodium hydride or cesium carbonate in an inert organic solvent such as dimethylformamide, acetonitrile or tetrahydrofuran, under an inert atmosphere such as argon to form compound of the invention Ia.

The above anion formation reaction is carried out employing a molar ratio of dihalide II':compound II of within the range from about 10:1 to about 0.5:1, preferably from about 2:1 to about 0.8:1.

Halide III is reacted with IV employing a molar ratio of IV:III within the range from about 10:1 to about 0.5:1, preferably from about 2:1, to about 0.8:1.

As seen in Scheme 1B, in accordance with another aspect of the present invention, the solution of compound II in an inert organic solvent, such as tetrahydrofuran, dioxane or diethyl ether, at a reduced temperature of within the range of from about −40° C. to about room temperature, is treated with base such as potassium hydroxide, potassium tert-butoxide, lithium or potassium bis(trimethylsilylamide), or n-butyllithium in an inert organic solvent such as hexane, tetrahydrofuran or diethyl ether, while maintaining temperature of the reaction mixture below from about −40° C. to about room temperature. The reaction mixture is treated with $R^1L^1$halide such as an alkylhalide, for example, 3-phenylpropylbromide to form the alkylated product Ia.

The above anion formation reaction is carried out employing a molar ratio of R¹L¹halide (II"):compound II of within the range from about 10:1 to about 0.5:1, preferably from about 2:1 to about 0.8:1.

Reaction Scheme 1C
Preparation of Starting Material II

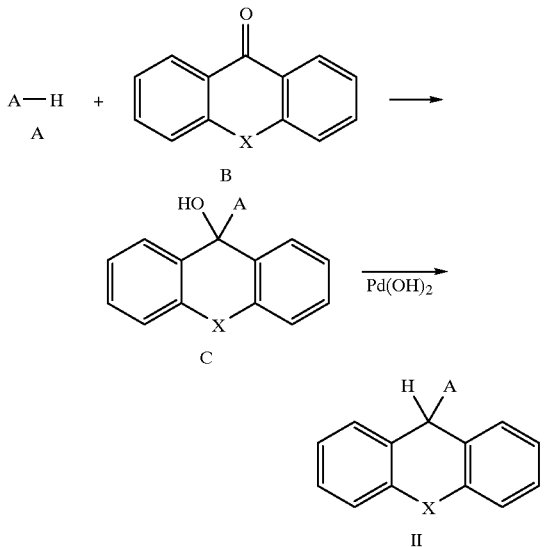

As seen in Scheme 1C, the starting compound II may be prepared by reacting ketone B and the anion of compound A. In an inert organic solvent such as tetrahydrofuran, dioxane or diethyl ether, at a reduced temperature within the range from about −78° C. to about 0° C., under an inert atmosphere such as argon, compound A is treated with an organic base such as n-butyllithium, lithium diisopropylamide or sec-butyllithium, preferably n-butyllithium, to form the anion of compound A. The ketone compound B is added to the anion of compound A at reduced temperature within the range from about −78° C. to about 0° C., preferably at −78° C., under an inert atmosphere such as argon, and the reaction is allowed to warm to a temperature within the range from about 0° C. to room temperature to give compound C. C is treated with Pd(OH)₂/C or Pd/C in the presence of cyclohexene in an inert organic solvent such as ethanol, or methanol with cyclohexene, preferably ethanol and cyclohexene mixture, while heating at a temperature within the range from about 78 to about 100° C., preferably from about 90 to about 100° C., to form II.

Conversely, C may be treated with Pd(OH)₂/C or Pd/C in the presence of hydrogen in an inert solvent to give II.

The reaction of A and B is carried out employing a molar ratio of A:B within the range from about 5:1 to about 0.8:1, preferably from about 2:1 to about 0.8:1.

Alternate Reaction Scheme 1C
Alternate Preparation of Starting Material II

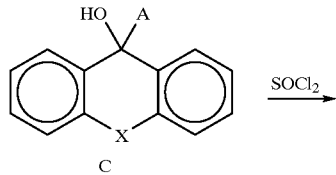

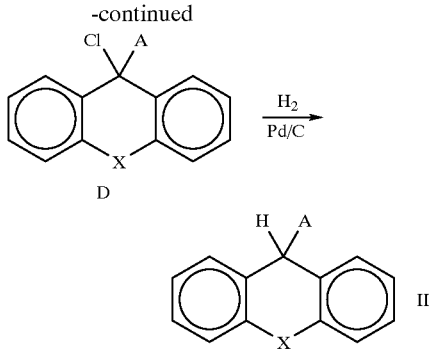

The starting compound II may also be prepared by treating alcohol C with an excess of thionyl chloride in an inert organic solvent such as toluene, benzene, or dichloromethane, preferably toluene, at a temperature range from about 0° C. to about 120° C., preferably from about 25 to about 110° C., to form D. D is treated with hydrogenation catalyst such as Pd/C or Pd(OH)₂/C in the presence of hydrogen gas in an inert organic solvent such as ethanol, methanol, or ethyl acetate, preferably ethanol, to form II.

Reaction Scheme 2

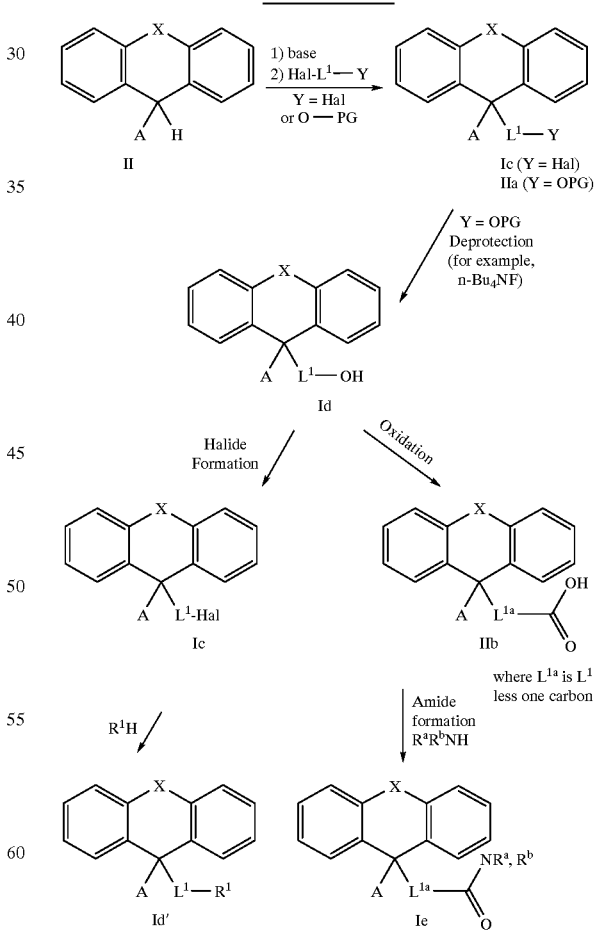

where PG is an oxygen protecting group, such as t-Bu(CH₃)₂Si or t-Bu(Ph)₂Si—.

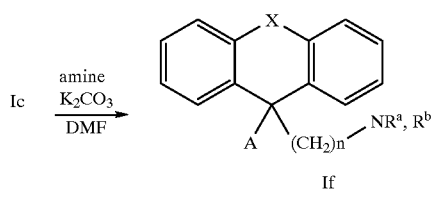

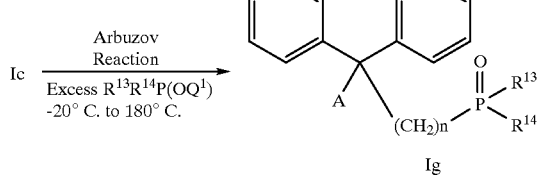

and $Q^1$ is alkyl, triorganosilyl (such as trimethylsilyl or t-butyldimethylsilyl), H, the latter in the presence of base such as butyllithium, sodium hydride, or sodium bis-(trimethylsilylamide)

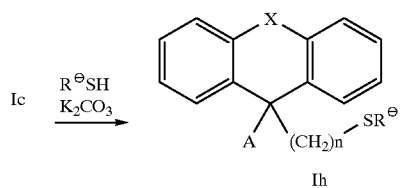

($R^e$ is alkyl, aryl, arylalkyl, heteroaryl, 2-benzthiazolyl), 2-imidazolyl)

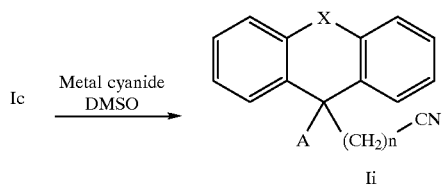

Scheme 2A
Alternate Scheme for Compound Ig

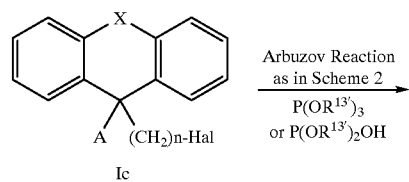

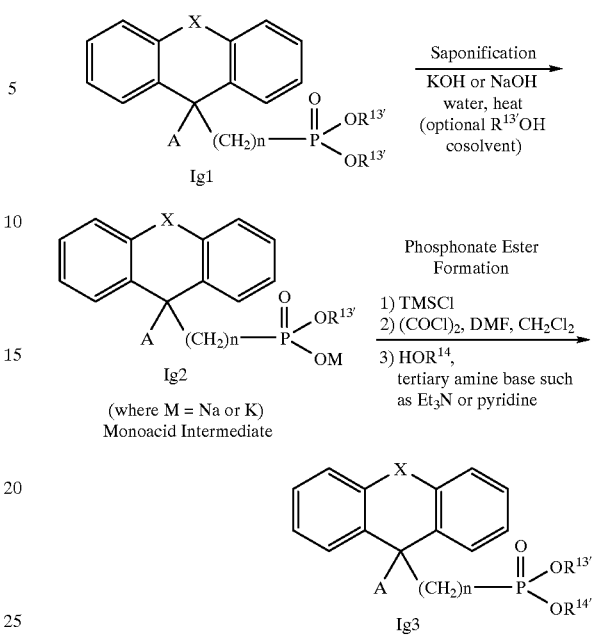

Scheme 2B

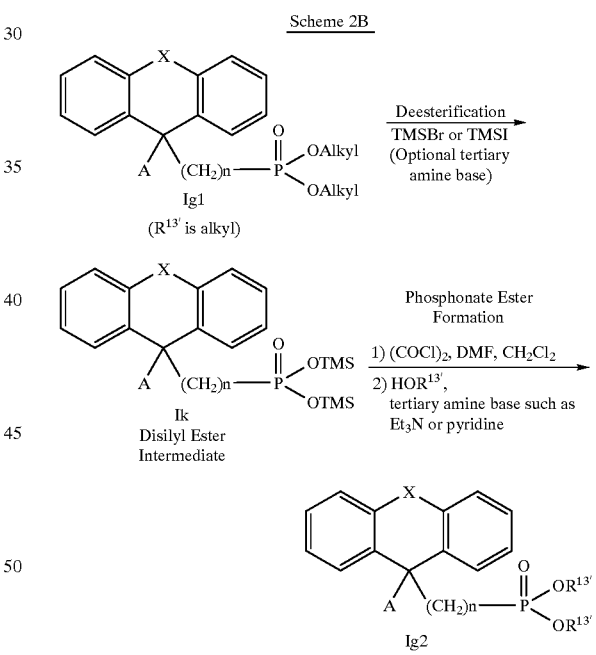

Scheme 3—Sulfur Oxidation (where A does not include S in its ring and X≠S)

Scheme 3
Sulfur Oxidation (where A does not include S in its ring and X≠S)

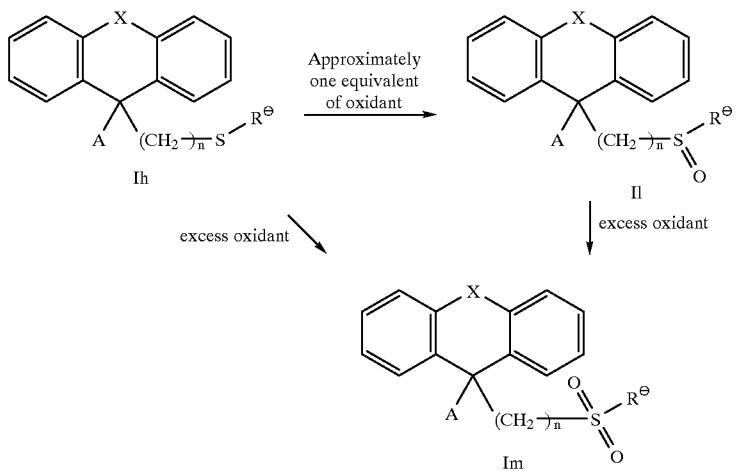

The above sulfur oxidations to the sulfoxide or sulfone are carried out by employing standard sulfur oxidation procedures in the art. Suitable oxidants include peracids (such as m-chloroperbenzoic acid) and sodium periodate.

Compounds I of the invention may be modified by the various transformations set out in Reaction Schemes 2, 2A, 2B and 3. Protected alcohol IIa can be converted into a wide variety of functional groups through the intermediacy of a halide Ic. For example, the alcohol Id can be converted to the halide Ic of the invention by either activation through the sulfonate ester (tosyl chloride, or mesyl chloride) and iodide displacement (NaI or KI in acetone or 2-butanone), or by reaction with triphenylphosphine, $I_2$ and imidazole. The iodide Ic can undergo an Arbuzov reaction to form phosphonates, phosphinates and phosphine oxides of the invention Ig. The Arbuzov reaction can be accomplished with phosphites, phosphinites, and phosphonites (for example, $R^{13}R^{14}POalkyl$ or $R^{13}R^{14}POSi(alkyl)_3$ or $R^{13}R^{14}POH$, the latter being in the presence of a base such as butyllithium, sodium hydride or sodium bis(trimethylsilylamide)) at temperatures within the range from about −20° C. to about 180° C. Alternately, displacement reactions to form amines If, thioethers Ih or nitriles Ii can be easily accomplished. To form amines If, halide Ic, can be treated with amines in DMF with or without $K_2CO_3$. Thioethers Ih can also be formed under similar conditions. The nitriles Ii are prepared from either KCN or NaCN in hot DMSO. The alcohol can also be oxidized to a carboxylic acid. The acids can also be used as intermediates to form amides of the invention Ie by methods previously described. The sulfur atom of Ih can be oxidized under standard conditions to sulfoxide Il or sulfone Im.

Reaction Scheme 4
Preparation of Acetals

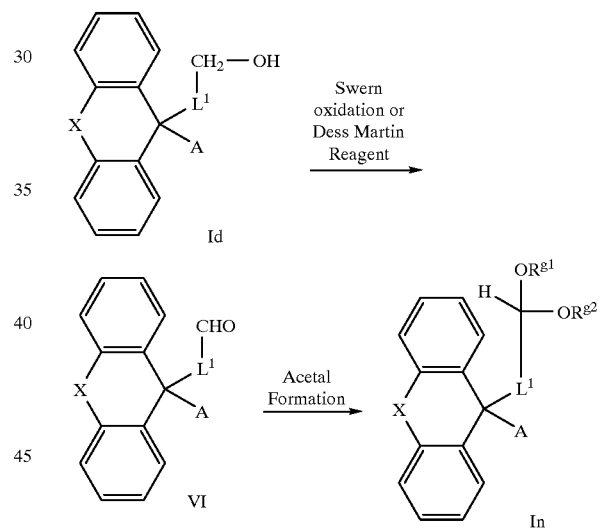

($R^{g1}$ and $R^{g2}$ are independently aryl, alkyl, and also where $R^{g1}$ and $R^{g2}$ are joined to form a ring, such as 1,3-dioxane)

Acetals of the invention In can be prepared from alcohol Id by oxidation of the alcohol to the aldehyde VI. Prefered reagents to accomplish the transformation are either the Swern oxidation (($COCl)_2$, DMSO, triethylamine) or Dess-Martin Periodinane. The aldehyde VI can be converted to the acetal In with excess alcohol such as 1,3-propanediol or ethylene glycol in the presence of a catalytic amount of acid such as $H_2SO_4$ or p-toluenesulfonic acid, optionally in the presence of a dehydrating agent such as 4A sieves or trimethyl orthoformate.

Reaction Scheme 5
Preparation of Compounds of Formula I where $R^1$ is Ar—M and $L^1$ is a linking group as defined above

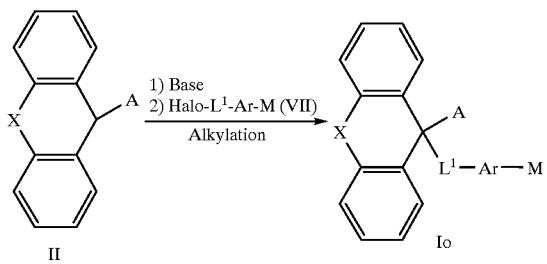

1) Ar or (Ar) is aryl or heteroaryl
2) M is $NO_2$, N—$PG^1$, $NHCOR^q$, $NHSO_2R^s$, $N(PG^2)COR^q$, or M is

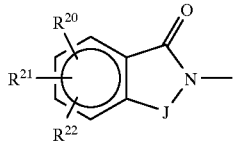

where $R^{20}$, $R^{21}$ and $R^{22}$ are previously defined, $N(PG^2)SO_2R^s$, where $R^q$ and $R^s$ are as defined in Scheme 10
Examples of protecting groups for nitrogen ($PG^1$) are Stabase
(—Si(CH$_3$)$_2$—CH$_2$CH$_2$—(CH$_3$)$_2$Si—), BOC (t-ButylO—CO—), bis-BOC or phthalimido.
3) Examples of $PG^2$ are BOC, $(CH_3)_3$Si— or t-Bu$(CH_3)_2$Si—

Compounds of the invention of formula I where $R^1$ is Ar-M can be prepared as shown in Reaction Scheme 5.

As seen in Scheme 5, compound II is treated with base and alkylated by reaction with halide VII, as described with respect to Scheme 1, to form alkylated compound Io.

Reaction Scheme 6
Preparation of Compound I, where $R^1$ is aryl or heteroaryl Scheme 6(A) where linking heteroatom T is a substituent on (Ar)

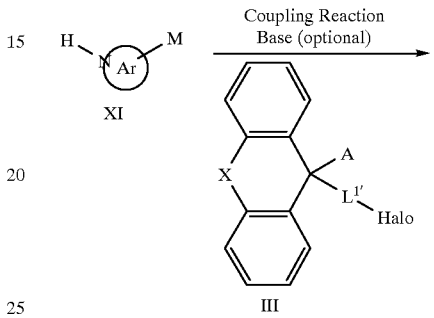

Sequence completed can be as in Scheme 10

M and (Ar) are defined as in Scheme 5.
T is either
1) a heteroatom (O, NH, N(alkyl) or S), as a substituent on (Ar) linked to (Ar) via the linker $L^{1''}$, where $L^{1''}$ can either be a bond, or is defined as is $L^1$, or (as depicted below)
2) a nitrogen atom, as a ring member of Ar, in which case $L^{1''}$ does not exist $L^{1'}$ is a linker such as defined for $L^1$, or a bond.

Note that the group-$L^{1'}$—T—$L^{1''}$-defines $L^1$.

Scheme 6(B) where the linking nitrogen is a ring member of (Ar)

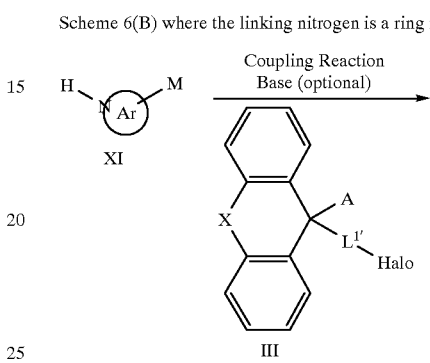

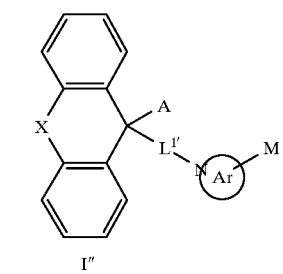

I''
Sequence completed as in Scheme 10

Compounds of the invention of formula I where $R^1$ is aryl or heteroaryl may be prepared as shown in Reaction Schemes 6(A) and 6(B).

In Scheme 6(A) compounds of formula I' (where $R^1$ is aryl or heteroaryl) may be prepared by coupling compound X with compound III, optionally in the presence of a base as described with respect to Scheme 1.

Compounds I' and I'' may be subjected to deprotection and/or further converted, where necessary as shown in Scheme 6.

In Scheme 6(B) compounds of formula I'' (where $R^1$ is heteroaryl and (Ar) is linked to $L^1$ via a ring nitrogen)) may be prepared by coupling XI with III, optionally in the presence of a base.

Reaction Scheme 7
Preparation of Compound I where $R^1$ is (Ar)

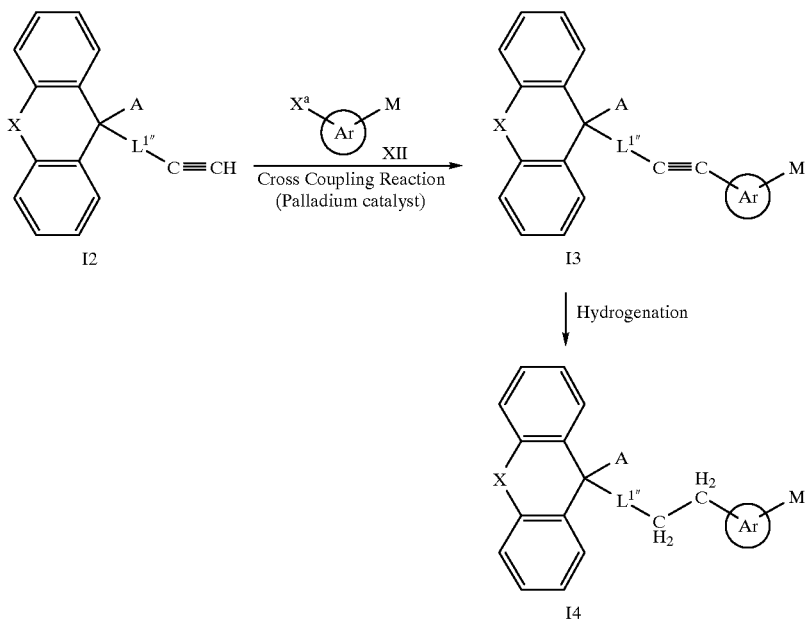

(Sequence can be completed as in Scheme 10)

$X^a$ is Bromo, iodo or trifluoromethanesulfonyloxy (Ar) is aryl or heteroaryl

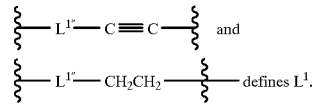 defines $L^1$.

Compounds of the invention of formula I where $R^1$ is (Ar) may be prepared as shown in Reaction Scheme 7.

In Scheme 7, acetylenic starting compound I2 is made to undergo a Castro-Stevens cross coupling with XII in the presence of a catalyst, such as palladium, $Pd(Ph_3P)_4$ or $Pd(Ph_3P)_2Cl_2$ in the presence of an amine (e.g. $BuNH_2$, $Et_3N$) and a Copper (I) salt (e.g. CuI) to form compound of the invention I3 and subjecting I3 to hydrogenation to form compound of the invention I4.

Compound I3 or I4 may be subjected to deprotection and further conversion if necessary, as described in Reaction Scheme 10.

Reaction Scheme 8
Alternate Preparation of Compound I where $R^1$ is (Ar)

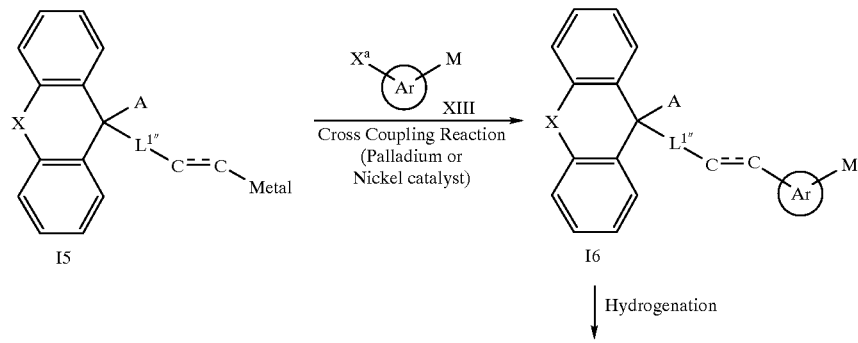

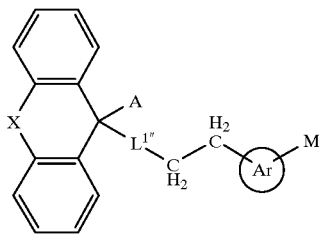

I4

Sequence can be completed as in Scheme 10

$X^a$ is Bromo, iodo or trifluoromethanesulfonyloxy (Ar) is aryl or heteroaryl

C═C represents a single or double C—C bond, and if a double bond can have either cis or trans stereochemistry.

Metal can be ZnHalo, MgHalo, $SnBu_3$, $B(alkyl)_2$, $B(OH)_2$

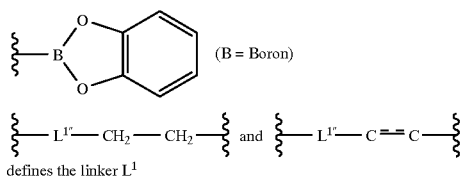

defines the linker $L^1$

In an alternative procedure as shown in Reaction Scheme 8, compound I4 may be prepared starting with compound I5 which is made to undergo a cross coupling reaction with XIII in the presence of a palladium or nickel catalyst, to form I6 which is hydrogenated to form I4.

Reaction Scheme 9
Preparation of Compound I where $L^1$ is an N-containing moiety

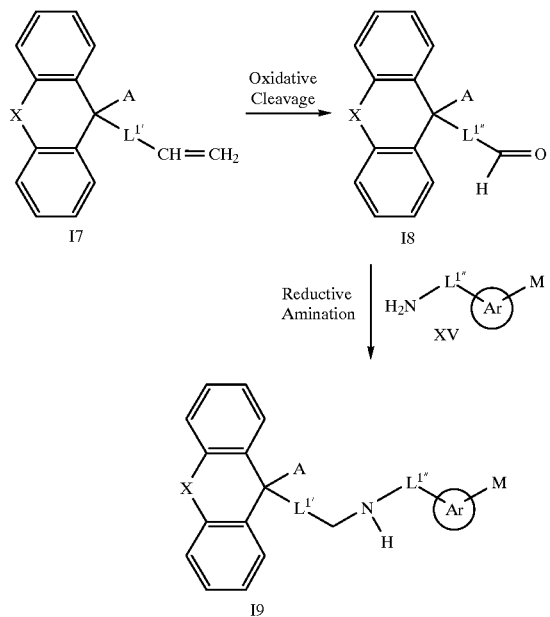

Sequence can be completed as in Scheme 10

Note that —$L^{1'}CH_2NHL^{1''}$ defines L

Oxidative Cleavage: Ozone in $CH_2Cl_2$ or $CH_3OH$, at low temperature (-78° C. to 25° C.) followed by reductive workup $Ph_3P$, $(CH_3)_2S$ or Zn, acetic acid; alternatively, use $NaIO_4$/$OsO_4$ in t-BuOH or THF, or mixtures with optional water added (Lemieux-Johnson reaction).

Reductive amination: $NaBH_4$, $NaBH_3CN$ or $NaB(OAc)_3H$, in $CH_2Cl_2$, MeOH, i-PrOH, T-BuOH, THF, DMF or mixtures thereof, optionally in the presence of an acid catalyst such as HCl or $Ti(OCH(CH_3)_2)_4$.

Compounds of the invention of formula I where $L^1$ is an N-containing moiety may be prepared as shown in Reaction Scheme 9 wherein starting compound I7 is made to undergo oxidative cleavage, as described above, to form aldehyde I8 which is subjected to reductive amination by reaction with amine XV, as described above, to form compound of the invention I9.

Compound I9 may undergo deprotection, if necessary, as shown in Scheme 10.

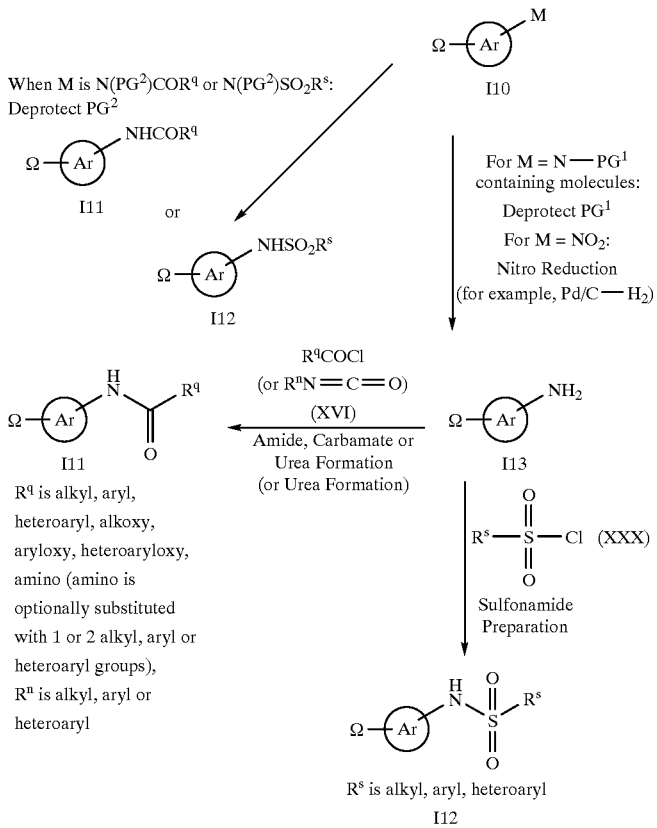

Reaction Scheme 10
Preparation of final products from M containing intermediates in Scheme 6 to 9

In a preferred method, superior yields of final products (I11 and I12) are obtained when the intermediate I13 is reacted with R$^q$COCl, R$^n$N=C=O or R$^s$SO$_2$Cl immediately after formation of I13 preferably in situ.

1) Ω represents

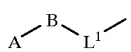

2) Ar is aryl or heteroaryl

3) M is NO$_2$, N-PG, NHCOR$^q$, NHSO$_2$R$^s$, N(PG$^2$)COR$^q$, N(PG$^2$)SO$_2$R

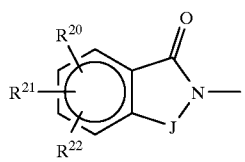

Examples of protecting groups for nitrogen (PG$^1$) are Stabase (—Si(CH$_3$)$_2$—CH$_2$CH$_2$—(CH$_3$)$_2$Si—), BOC (t-ButylO—CO—) and bis-BOC.

4) Examples of PG$^2$ are BOC, (CH$_3$)$_3$Si— or t-Bu(CH$_3$)$_2$Si—

5) Deprotection according to the prior art.

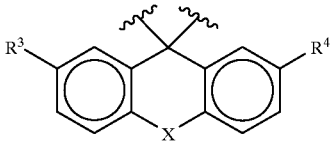

X is a bond, oxygen or sulfur;

R$^3$ and R$^4$ are the same or different and are H or F;

R$^1$ is aryl, phenyl, heteroaryl, imidazolyl, cycloheteroalkyl, pyridyl, cyclohexyl, PO(R$^{13}$) (R$^{14}$), heteroarylthio, benzthiazole-2-thio, benzimidazolyl, indolyl, imidazole-2-thio, alkyl, alkenyl or 1,3-dioxan-2-yl, wherein each of the above is optionally substituted;

L$^1$ is a chain containing 1 to 5 atoms in a linear chain; and
A is

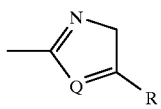

where Q is S or N-alkyl and R is H or alkyl.

More preferred are compounds of formula I where B is

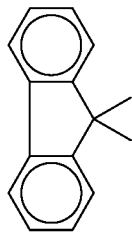

A is

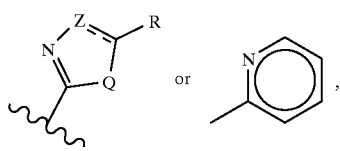

where Z is CH;

Q is

where R⁵ is alkyl such as methyl or ethyl;
------ is a double bond;
R is H or alkyl such as methyl;
L¹ is alkylene of 2–5 carbons in the chain; and
R¹ is

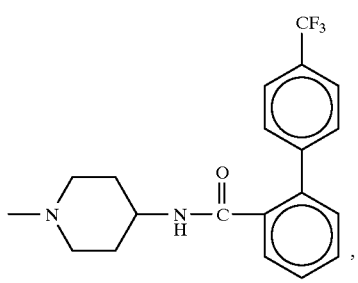

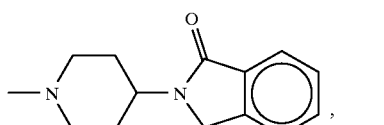

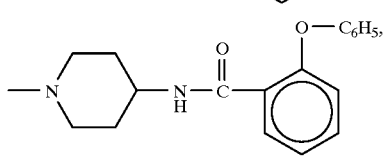

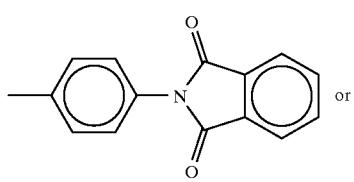 or

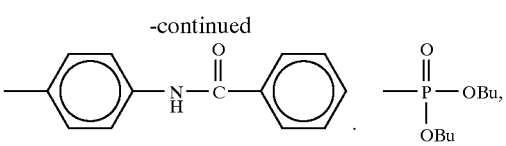

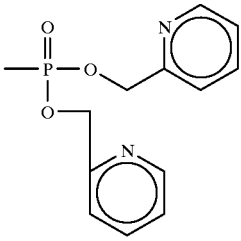

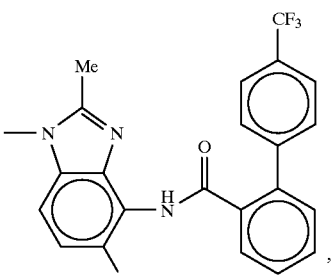

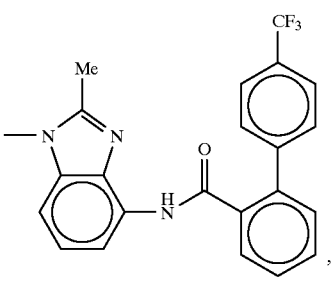

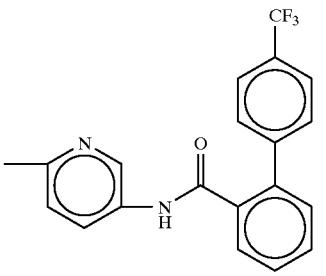

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, employing MTP isolated from one of the following sources:

(1) bovine liver microsomes,
(2) HepG$_2$ cells (human hepatoma cells) or
(3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the activity of MTP and therefore decrease serum cholesterol and TG levels, and TG, fatty acid and cholesterol absorption and thus are useful in treating hypercholesterolemia, hypertriglyceridemia, hyperlipidemia, pancreatitis, type 2 diabetes, hyperglycemia and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day, preferably, from about 10 to about 400 mg per day in single or divided doses of one to four times daily.

The following Examples represent preferred embodiments of the invention. All temperatures are in °C. unless indicated otherwise.

EXAMPLE 1

2,3-Dihydro-2-[1-[4-[9-(5-methyl-2-thiazolyl)-9H-fluoren-9-yl]butyl]-4-piperidinyl]-1H-isoindol-1-one

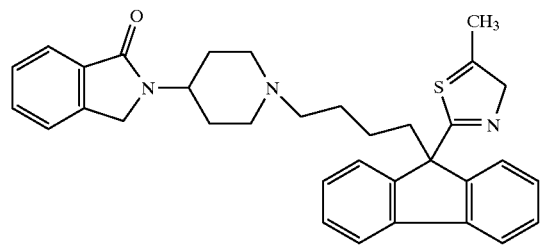

A.

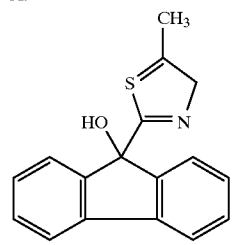

A solution of 5-methylthiazole (0.992 g, 10 mmol) in 20 mL of dry tetrahydrofuran was cooled to −78° C. under an argon atmosphere and n-butyllithium (4 mL of a 2.5 M solution in hexane) was added. The reaction was stirred at −78° C. for 30 min. and a solution of fluorenone (1.80 g, 10 mmol) in 5 mL of THF was slowly added. The reaction was stirred at −78° C. for 1 hour and then allowed to warm to room temperature for 1 hour. The reaction was quenched with 1 N HCl and extracted with ethyl acetate (3×30 mL). The combined extract was washed with sodium bicarbonate, brine and dried over sodium sulfate. The solvents were evaporated and the crude product crystallized from hot ethanol yielding 2.63 grams (94%) of title compound as pale yellow crystals, m.p. 166–168° C., [CI Mass Spec. (M+H)$^+$=280$^+$].

B.

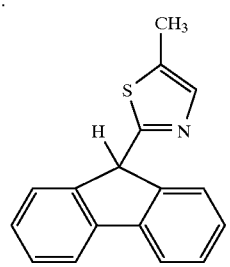

To a solution of Part A compound (1.0 g, 3.6 mmol) in 20 mL of ethanol and 10 mL of cyclohexene was added 500 mg of 20% palladium hydroxide on carbon and the mixture was then heated at 80° C. for 48 hrs. The reaction was filtered and the solvents evaporated yielding the crude product as a colorless solid. Crystallization from ethyl acetate/hexane yielded 640 mg (68%) of title compound as a colorless solid, [CI Mass Spec (M+H)$^+$=264$^+$].

C.

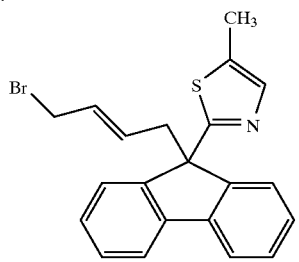

A solution of Part B compound (263 mg, 1 mmol) in 3 mL of dry tetrahydrofuran was cooled to 0° C. under an argon atmosphere and n-butyllithium (0.4 mL of a 2.5 M solution in hexane) was added. The reaction was stirred for 30 min. at 0° C. and was then added to a cold (0° C.) solution of 1,4-dibromo-2-butene (856 mg, 4 mmol) in 5 mL of THF. The mixture was stirred at 0° C. for 1 hr and was then allowed to warm to room temperature and stirred for 1 hr longer. The reaction was quenched with 5 mL of 1 N HCl and extracted with ethyl acetate (3×10 mL). The combined extract was washed with water, brine and dried over sodium sulfate. The solvents were evaporated and the crude residue was purified on a Merck EM silica column eluting with 5% isopropyl alcohol/dichloromethane yielding 172 mg (44%) of title compound as a colorless solid, [Electrospray Mass Spec. (M+H)$^+$=396$^+$].

D.

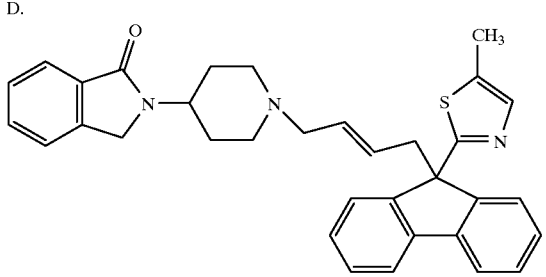

A mixture of Part C compound (158 mg, 0.4 mmol),

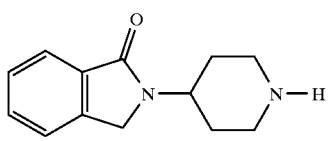

(89 mg, 0.41 mmol) and potassium carbonate (62 mg, 0.45 mmol) in 2 mL of dimethylformamide was stirred at room temperature for 18 hrs under an argon atmosphere. The mixture was diluted with 10 mL of water and extracted with ethyl acetate (3×15 mL). The combined extract was washed with water (4×25 mL), brine and dried over sodium sulfate. The solvents were evaporated and the crude product was purified on a Merck EM silica column eluting with 0 to 10% gradient of isopropyl alcohol/dichloromethane yielding 146 mg (70%) of title compound as a colorless solid, m.p. 154–156° C., [Electrospray Mass Spec. (M+H)$^+$=532$^+$].

E.

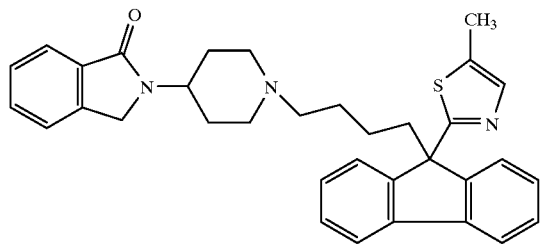

A solution of Part D compound (140 mg, 0.26 mmol) in 8 mL of ethanol containing 75 mg of 10% Pd/C for catalyst was stirred under a hydrogen atmosphere (balloon) for 18 hrs. The reaction was filtered through a 0.2 μm nylon filter to remove the catalyst and the solvent evaporated yielding 133 mg (96%) of title compound as a colorless solid, m.p. 146–148° C.

Anal Calc'd for $C_{34}H_{35}N_3SO+0.54\ H_2O$ (MW 543.46):

C, 75.14; H, 6.69; N, 7.70; S, 5.90

Found: C, 75.14; H, 6.72; N, 7.33; S, 6.17.

EXAMPLE 2

[4-[9-(1-Methyl-1H-imidazol-2-yl)9H-fluoren-9-yl]-butyl]phosphonic acid, dibutyl ester

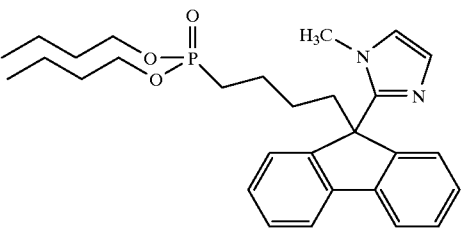

A.

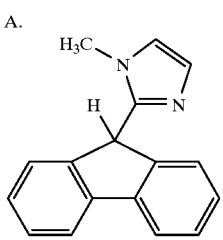

A(1).

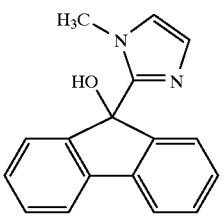

A solution of 1-methylimidazole (4.11 g, 50 mmol) in 40 mL of dry tetrahydrofuran was cooled to −78° C. under an argon atmosphere and n-butyl lithium (20 mL of a 2.5 M solution in hexane) was added. The reaction was stirred at −78° C. for 30 min. and a solution of fluorenone (9.0 g, 50 mmol) in 10 mL of THF was slowly added. The reaction was stirred at −78° C. for 1 hr and then allowed to warm to 0° C. for 1 hour. The reaction was quenched with saturated ammonium chloride and extracted with ethyl acetate (3×40 mL). The combined extract was washed with brine and dried over sodium sulfate. The solvents were evaporated and the crude product crystallized from hot ethanol yielding 11.2 g (85%) of title compound as pale yellow crystals, m.p. 174–176° C.,
[CI Mass Spec. (M+H)$^+$=263$^+$].

A(2).

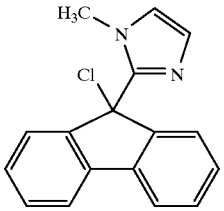

A solution of Part A(1) compound (11 g, 42 mmol) in toluene containing thionyl chloride was heated at reflux for 2 hrs, cooled to room temperature and the solvents evaporated yielding 13.77 g (99%) of the title chloro intermediate (HCl salt) as a pale yellow solid, [Mass Spec. (M+H)⁺= 281⁺].

A(3).

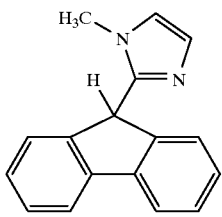

A solution of Part A(2) compound (11 g, 34 mmol) in 200 mL of ethanol containing 2.5 g of 10% palladium on carbon was stirred under a hydrogen atmosphere (balloon) for 24 hrs. The catalyst was removed by filtration and the solvents evaporated yielding 9.6 g (98%) of the 9-hydro intermediate as a brown oil which solidified upon standing, [Mass Spec. (M+H)⁺=247⁺].

Note: The free-base of A(3) was prepared by partitioning with 1 N sodium hydroxide and dichloromethane. The organic layer was dried over sodium sulfate and evaporation of the solvents yielded the free-base as a brown solid which was used without further purification.

B.

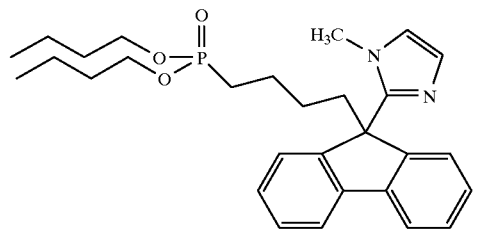

A solution of Part A compound (493 mg, 2 mmol) in 5 mL of dry THF was cooled to 0° C. under an argon atmosphere and 1 equiv. of a 2.5 M n-butyllithium solution in hexane (0.8 mL) was added and the resulting mixture was stirred at 0° C. for 20 min. 4-Iodobutyl-di-n-butyl phosphate was added and the mixture was stirred at 0° C. for 2.5 hrs. The reaction was quenched with saturated ammonium chloride solution, extracted with ethyl acetate (3×20 mL) and dried over sodium sulfate. The solvent was evaporated yielding 880 mg of crude material which was purified on a Merck silica column eluting with a gradient of 5 to 10% methanol/ dichloromethane+0.1% ammonium hydroxide. Evaporation of solvents yielded 146 mg (16%) of title compound as light brown solid, m.p. 120–122° C.

Anal Calc'd for $C_{29}H_{39}H_2PO_3+0.09\ H_2O$ (MW 496.22):

C, 70.19; H, 7.96; N, 5.64; P, 6.24

Found: C, 70.16; H, 7.61; N, 5.68; P, 6.28.

EXAMPLE 3

N-[4-[4-[9-(1-Methyl-1H-imidazol-2-yl)-9H-fluoren-9-yl]butyl]phenyl]benzamide

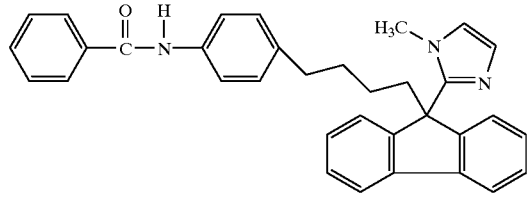

A.

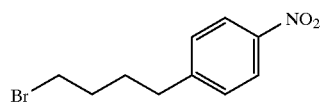

A solution of 4-(4-nitrophenyl)-1-butanol (3.90 g, 20 mmol) in 70 mL of dichloromethane was cooled to 0° C. under an argon atmosphere and triphenylphosphine (5.77 g, 22 mmol) was added followed by the addition of N-bromosuccinimide (3.92 g, 22 mmol). The reaction mixture was allowed to warm to ambient temperature and stir for 2.5 hrs. The reaction was washed with saturated sodium bisulfite, water, brine and dried over sodium sulfate. The solvent was evaporated yielding the crude product as a dark yellow oil. Purification on a Merck EM silica column eluting with 25% dichloromethane/hexanes yielded 4.3 g (84%) of title compound as a pale yellow oil.

B.

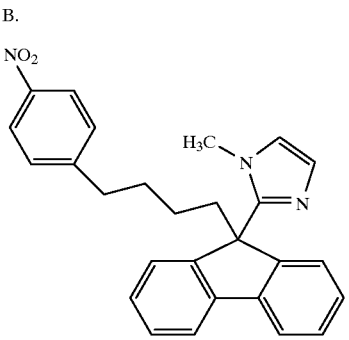

A solution of 9-(2-(1-methylimidazole))-9H-fluorene (prepared as in Example 2 Part A) in 15 mL of THF was cooled to 0° C. under an argon atmosphere and a 2.5 M solution of n-butyl lithium (2.1 mL, 5.25 mmol) was added. The mixture was stirred at 0° C. for 0.5 hr and Part A compound (1.42 g, 5.5 mmol) was added. The reaction was then allowed to warm to ambient temperature and stirred overnight. The reaction was quenched with saturated ammonium chloride and extracted with ethyl acetate (3×20 mL). The combined extract was washed with water, brine and dried over sodium sulfate. Evaporation of the solvents yielded the crude product as a black oil. Purification on Merck EM silica eluting with ethyl acetate/hexane yielded 560 mg of title compound (27%) as a pale yellow solid, m.p. 146–148° C. [ES Mass Spec. (M+H)⁺=424⁺].

C.

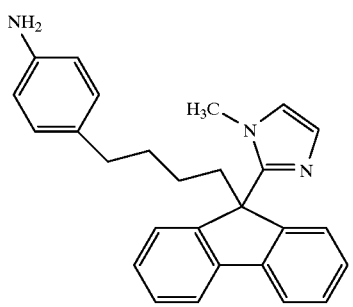

A solution of Part B compound (540 mg, 1.28 mmol) in 15 mL of ethanol containing 10% palladium on carbon as catalyst was stirred under a hydrogen atmosphere (balloon) for 12 hrs. The catalyst was removed by filtration and the ethanol was evaporated yielding 500 mg (99%) of the title amine as a colorless foam. [ES Mass Spec. (M+H)$^+$=394$^+$].

D. N-[4-[4-[9-(1-Methyl-1H-imidazol-2-yl)-9H-fluoren-9-yl]butyl]phenyl]benzamide To a solution of Part C compound (212 mg, 0.54 mmol) and triethylamine (101 mg, 1 mmol) in 4 mL of dichloromethane was added benzoyl chloride (113 mg, 0.81 mmol) at 0° C. under an argon atmosphere. After stirring for 3 hrs at 0° C. the mixture was diluted with dichloromethane and washed with 0.1 N hydrochloric acid, water, brine and dried over sodium sulfate. The solvent was evaporated yielding the crude product as a colorless solid. Purification on a Merck EM silica column eluting with 5% methanol/dichloromethane yielded 210 mg (76%) of title compound as a colorless solid, m.p. 210–212° C.

Anal Calc'd for $C_{34}H_{31}N_3O+1.9\ H_2O$ (MW 531.46):

C, 79.26; H, 6.79; N, 8.16
Found: C, 79.29; H, 6.53; N, 8.13.

EXAMPLE 4

2-[4-[4-[9-(1-Methyl-1H-imidazol-2-yl)-9H-fluoren-9-yl]butyl]phenyl]-1H-isoindole-1,3(2H)-dione

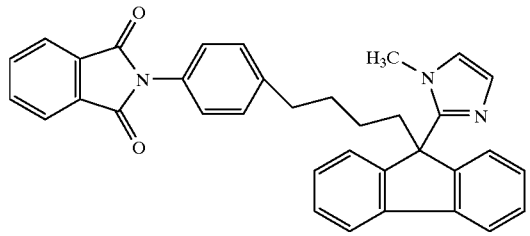

A mixture of Example 3 Part C compound (212 mg, 0.54 mmol) and phthalic anhydride (88 mg, 0.6 mmol) was heated neat at 140° C. for 30 min. The crude product was purified on a Merck EM silica column eluting with 5% methanol/dichloromethane yielding 262 mg (92%) of title compound as a colorless solid, m.p. 76–80° C.

Anal Calc'd for $C_{35}H_{29}N_3O_2+H_2O$ (MW 527.20):

C, 79.71; H, 5.62; N, 7.97
Found: C, 79.83; H, 5.59; N, 7.85.

The following compounds were prepared employing the procedures set forth herein and in Examples 1 to 4.

EXAMPLE 5

Example 5

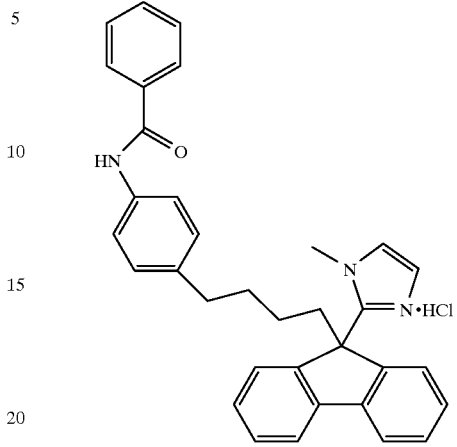

N-[4-[4-[9-(1-Methyl-1H-imidazol-2-yl)-9H-fluoren-9-yl]butyl]phenyl]benzamide, monohydrochloride M.S (electrospray,+ions); m/z 498 (M+H); Anal Calc'd for $C_{34}H_{31}N_3O.0.8\ HCl.0.09\ EtOAc.0.07\ Et_2O, 1.25\ H_2O$: C, 73.97; H, 6.40; N, 7.47; Cl, 5.19 Found: C, 74.08; H, 6.29; N, 7.33; Cl, 5.05.

EXAMPLE 6

Example 6

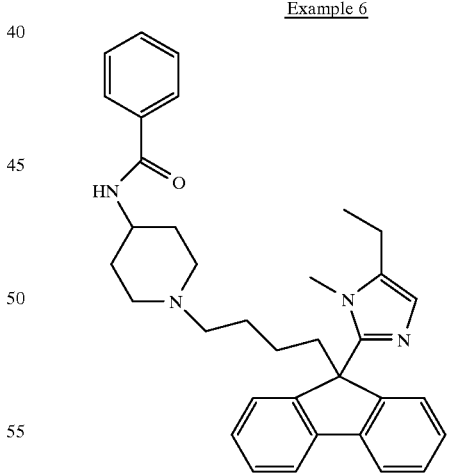

N-[1-[4-[9-(5-Ethyl-1-methyl-1H-imidazol-2-yl)-9H-fluoren-9-yl]butyl]-4-piperidinyl]benzamide M.S (electrospray, M+H)$^+$; m/z 533$^+$; Anal. Calc'd for $C_{35}H_{40}N_4O.0.65\ H_2O.0.09\ DMF$: C, 76.88; H, 7.67; N, 10.40 Found: C, 76.83; H, 7.61; N, 10.40.

EXAMPLE 7

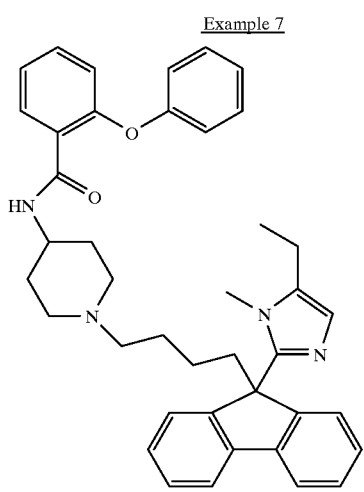

N-[1-[4-[9-(5-Ethyl-1-methyl-1H-imidazol-2-yl)-9H-fluoren-9-yl]butyl]-4-piperidinyl-2-phenoxybenzamide M.S. (electrospray, M+H)⁺; m/z 625⁺;

EXAMPLE 8

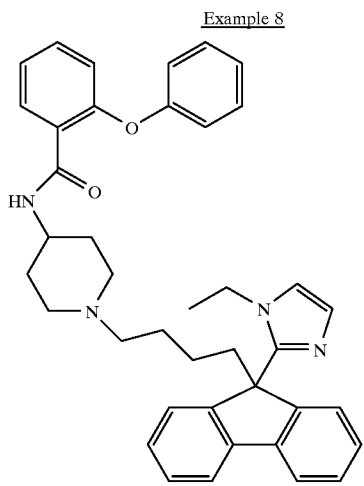

N-[1-[4-[9-(1-Ethyl-1H-imidazol-2-yl)-9H-fluoren-9-yl]butyl]-4-piperidinyl]-2-phenoxybenzamide M.S. (electrospray,+ions); m/z 611 (M+H);

EXAMPLE 9

N-[1-[4-[9-(1-Ethyl-1H-imidazol-2-yl)-9H-fluoren-9-yl]butyl]-4-piperidinyl]-2-phenoxybenzamide

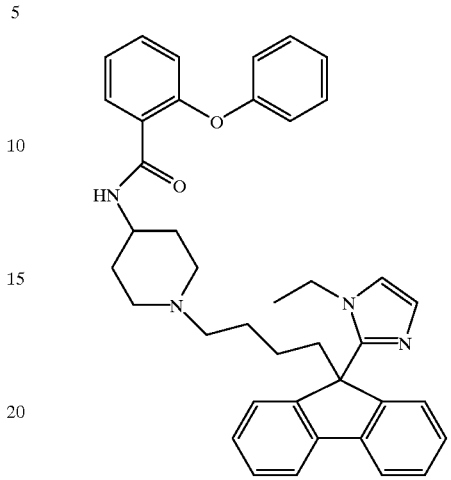

A.

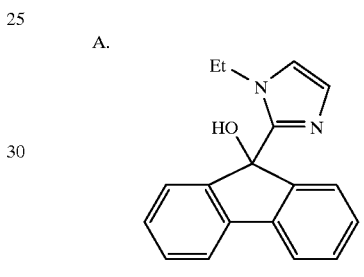

A solution of 1-ethylimdazole (5.0 g, 52 mmol) in THF (50 ml) was cooled to −78° C. under an argon atmosphere and n-butyllithium (21 ml, 2.5 N solution in hexane) was added dropwise over 15 min. After 30 min., a solution of fluorenone (9.35 g, 52 mmol) in THF (14 ml) was added dropwise over 15 min. The heterogeneous reaction mixture was stirred at −78° C. for 45 min and then allowed to warm to 0° C. for 1.5 hr. The reaction was quenched with saturated ammonium chloride, extracted with ethyl acetate, the organic layer washed with brine, dried over sodium sulfate, and concentrated in vacuo to a slightly yellow colored solid. The crude product crystallized from hot ethanol yielding 10.6 g of title compound as a colorless solid, Rf=0.42 (Silica gel, 10% methanol:dichloromethane).

B.

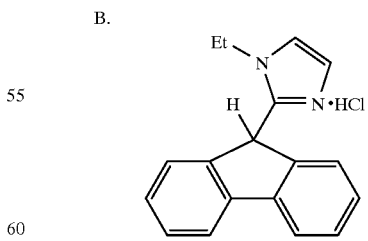

A solution of Part A compound (9.5 g, 34 mmol) in toluene containing thionyl chloride (15.5 ml, 0.21 mol) was heated at reflux for 3 hrs, cooled to room temperature and the solvents evaporated in vacuo to give 16.0 g (>100% crude recovery, contaminated with toluene) of a pale yellow

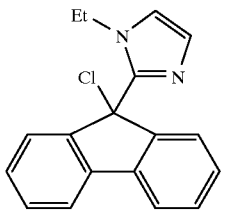

foam containing the chloro intermediate (HCl salt).

A solution of the chloro intermediate (5.1 g, ≦10.9 mmol) in ethanol (70 ml) containing 10% palladium on carbon (0.88 g) was stirred under a hydrogen atmosphere (balloon) for 24 hrs. The catalyst was removed by filtration and the solvents evaporated to give an orange colored foam (3.7 g, >100% crude recovery) containing title intermediate, MS (CI,+ions) m/z 261 (M+H).

C.

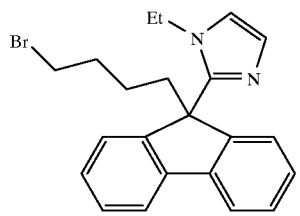

A suspension of Part B intermediate (1.0 g, 3.4 mmol) in THF (8 ml) was cooled to −78° C. and degassed with argon. At 0° C., n-butyllithium (3 ml, 2.5 M solution in hexanes) was added and the resulting mixture was stirred at 0° C. for 30 m in. Tetrabutylammonium iodide (130 mg, 0.35 mmol) was added to the reaction mixture followed by the addition of 1,4-dibromobutane (0.46 ml, 3.9 mmol). The reaction was brought immediately to room temperature for 5 hrs then quenched with saturated ammonium chloride and stored at −80° C. overnight. After warming, the aqueous layer was extracted with ethyl acetate, the organics washed with saturated NaHCO$_3$, brine, dried over sodium sulfate, and the volatiles evaporated in vacuo. The residue was purified by flash chromatography (SilicAr CC-7, 150 g), eluting with 2% methanol/dichloromethane containing 0.1% ammonium hydroxide to give title compound as a brown oil (274 mg), MS (electrospray,+ions) m/z 395 (M+H).

D.

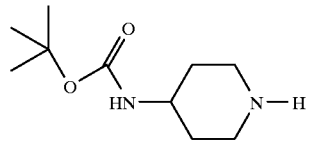

To a dichloromethane (400 ml) solution at 0° C. of 4-amino-1-benzylpiperidine (44.8 g, 235 mmol) is added slowly a dichloromethane (75 ml) solution of di-tert-butyl dicarbonate (55.9 g, 256 mmol). After 1.15 h at room temperature, the reaction mixture was evaporated in vacuo and triturated twice with ether to give an intermediate as a colorless solid (61 g).

To a suspension of the above intermediate (10 g, 34.4 mmol) in ethanol (75 ml) and cyclohexene (15 ml) is added Pearlman's catalyst (1 g, 20% Pd(OH)$_2$/Carbon) and the mixture refluxed for 2.1 h. After cooling, the mixture was filtered through Celite, washing with ethanol, to give title compound (7 g) as a colorless solid.

E.

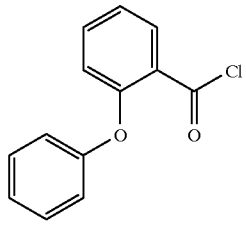

To a dichloromethane (50 ml) solution of o-phenoxybenzoic acid (3.8 g, 17.7 mmol) is added oxalyl chloride (2.33 ml, 26.7 mmol) and DMF (0.1 ml). After 1.5 h the reaction mixture was evaporated in vacuo to give an oily solid residue. The residue was partially dissolved in hexanes, the solid removed by filtration, and the volatiles removed in vacuo to give title compound (3.63 g) as a colorless solid.

F.

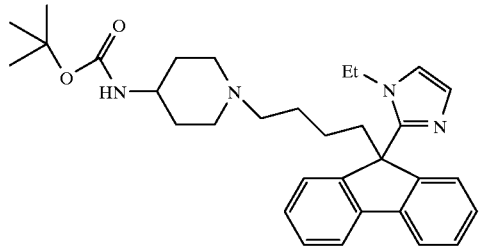

A solution of Part C compound (250 mg, 0.63 mmol), Part D compound (150 mg, 0.75 mmol) and potassium carbonate (113 mg, 0.82 mmol) in DMF (3 ml) was stirred at room temperature under argon for 63 h. The reaction mixture was diluted with saturated sodium bicarbonate and extracted twice with ethyl acetate. The combined organics were washed with water, the aqueous layer extracted again with ethyl acetate, and the organics dried over sodium sulfate. The solvent was evaporated and the crude product was purified twice by flash chromatography (SilicAr CC-7, 3×15 cm), eluting with 6.5% methanol/dichloromethane containing 0.6% ammonium hydroxide to give impure title compound (120 mg, 85% pure by HPLC), MS (electrospray,+ions) m/z 515 (M+H).

G. N-[1-[4-[9-(1-Ethyl-1H-imidazol-2-yl)-9H-fluoren-9-yl]butyl]-4-piperidinyl]-2-phenoxy-benzamide To neat Part F compound (120 mg, ≦0.23 mmol) was added HCl (1.5 ml, 4N in dioxane) and the mixture stirred for 1.5 h. The volatiles were removed in vacuo to give an intermediate as a colorless solid, used immediately in the subsequent reaction.

To a THF (1.5 ml) solution of the above intermediate (≦0.23 mmol) is added triethylamine (0.16 ml) and a THF (0.5 ml) solution of Part E compound (70 mg, 0.3 mmol). The cloudy reaction mixture was quenched with saturated sodium bicarbonate after stirring at room temperature overnight. The aqueous layer was extracted twice with ethyl acetate, the organics dried over sodium sulfate, and evaporated to give an oily solid (200 mg). The residue was purified by flash chromatography (silica gel, 50 ml), eluting with 4% methanol/dichloromethane containing 0.4% ammonium hydroxide, then 5% methanol/dichloromethane containing 0.5% ammonium hydroxide to give title compound as a colorless foam (50 mg), MS (electrospray,+ions) m/z 611 (M+H).

EXAMPLE 10

[3-[9-(2-Pyridinyl)-9H-fluoren-9-yl]propyl] phosphonic acid, dibutyl ester

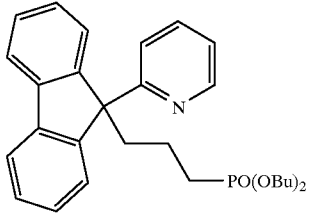

A.

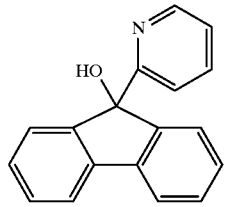

To a stirred solution of 2-bromopyridine (1.2 ml, 13 mmol) in diethyl ether (20 ml) at –78° C. was added n-butyllithium (5.1 ml, 2.5 M in hexanes). The mixture was stirred for 0.5 h under argon at –78° C. and a solution of fluorenone (2.3 g, 13 mmol) in diethyl ether (50 ml) was then added dropwise. The reaction was stirred at –78° C. for 4h, stored at –40° C. overnight, then stirred for 1 h at room temperature. The reaction was partitioned between water and ethyl acetate, the organic layer was washed once with water, once with brine, dried (sodium sulfate) and the solvent removed in vacuo to give a yellow oil. The residue was purified by flash column chromatography on silica gel (330 g) eluted with 10–20% ethyl acetate in hexanes to give title compound as a colorless solid (2.01 g, 61% yield). mp: 126.5–128.5° C.

B.

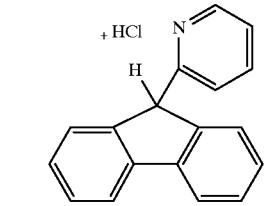

B(1).

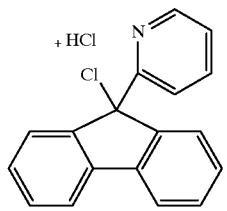

Part A compound (1.0 g, 3.8 mmol) was dissolved in thionyl chloride (10 ml) at 0° C. The ice bath was removed and the reaction was heated to 60° C. under argon for 1 h. The volatiles were removed in vacuo to give the unstable Part B(1) compound, which was used as is in the subsequent reaction.

The above residue was dissolved in ethanol (5 ml) and methanol (5 ml), 10% palladium on carbon (500 mg) was added, and the reaction stirred in a hydrogen atmosphere (balloon) overnight. The reaction was filtered through Celite, rinsed with methanol, and the filtrate was concentrated in vacuo to give the title compound as a yellow solid (500 mg, 46.3% yield)

C.

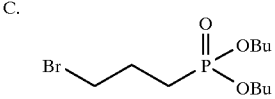

Freshly distilled tributylphosphite (34 ml, 126 mmol) and freshly distilled 1,3-dibromopropane (127.9 ml, 1.26 mol) were combined a nd heated at 120° C. for 16 h. The excess 1,3-dibromopropane was removed by distillation to give the title compound as a yellow oil (29 g, 74% yield).

D.

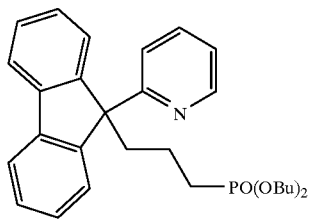

A solution of Part B compound (500 mg, 1.8 mmol) in tetrahydrofuran (10 ml) was cooled to 0° C., n-butyl lithium (1.0 ml, 2.5M in hexanes) was added, and the reaction stirred at 0° C. under argon for 1 h. Part C compound (590 mg, 1.8 mmol) was then added, and the reaction stirred 2 h at 0° C. under argon. The reaction was quenched with saturated ammonium chloride and stored at –40° C. for two weeks. After warming to room temperature, the mixture was extracted twice with ethyl acetate, the combined organic layers dried (sodium sulfate) and the solvent removed in vacuo to give a dark oily residue. The residue was purified by flash column chromatography on silica gel (80 g) eluted with 10% ethyl acetate in hexanes to 100% ethyl acetate to give the title compound as a yellow oil (132 mg, 15.5% yield).

MS: (ESI,+ions) m/z 478 (M+H).

EXAMPLE 11 to 74

Following are additional preferred examples of compounds of the invention which may be prepared employing procedures described hereinbefore.

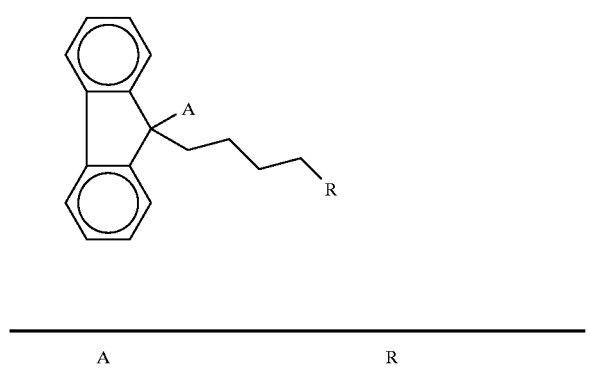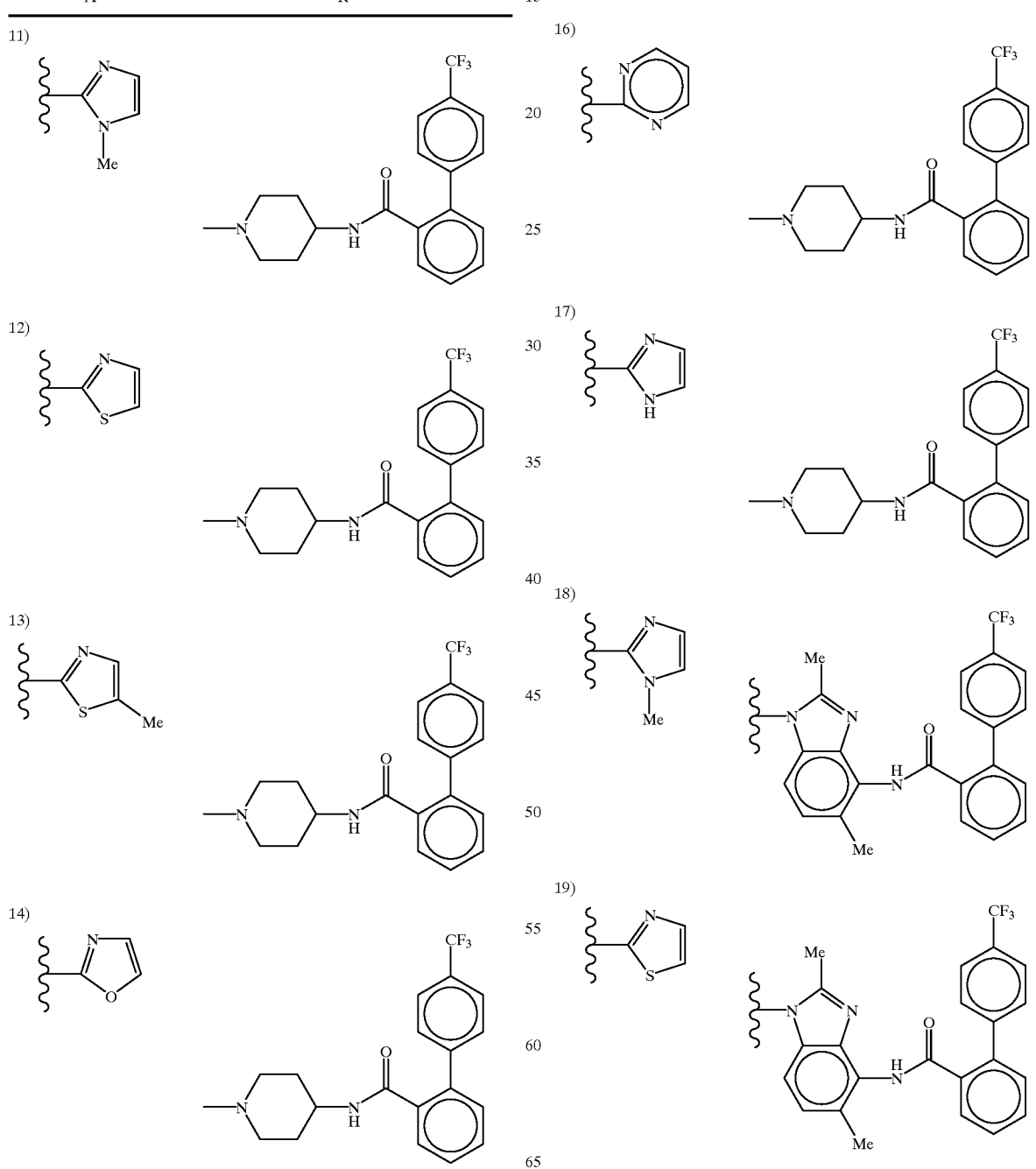

| A | R |
|---|---|
| 20) 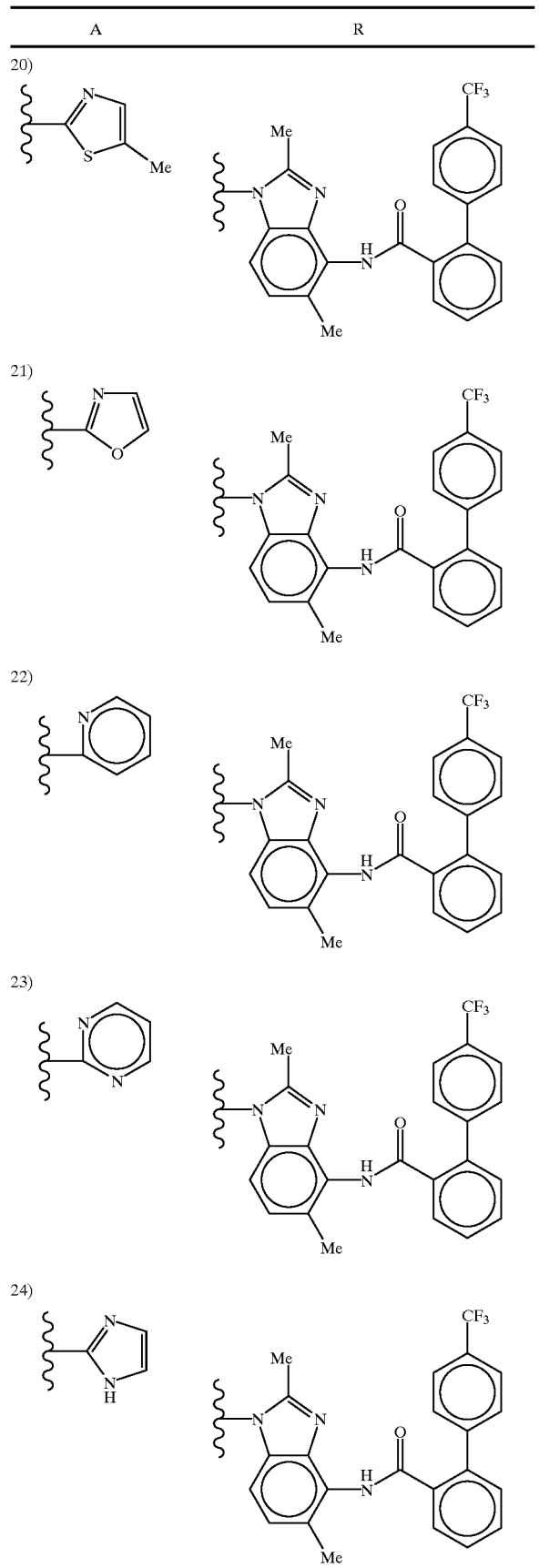 | |
| 21) | |
| 22) | |
| 23) | |
| 24) | |
| A | R |
|---|---|
| 25) 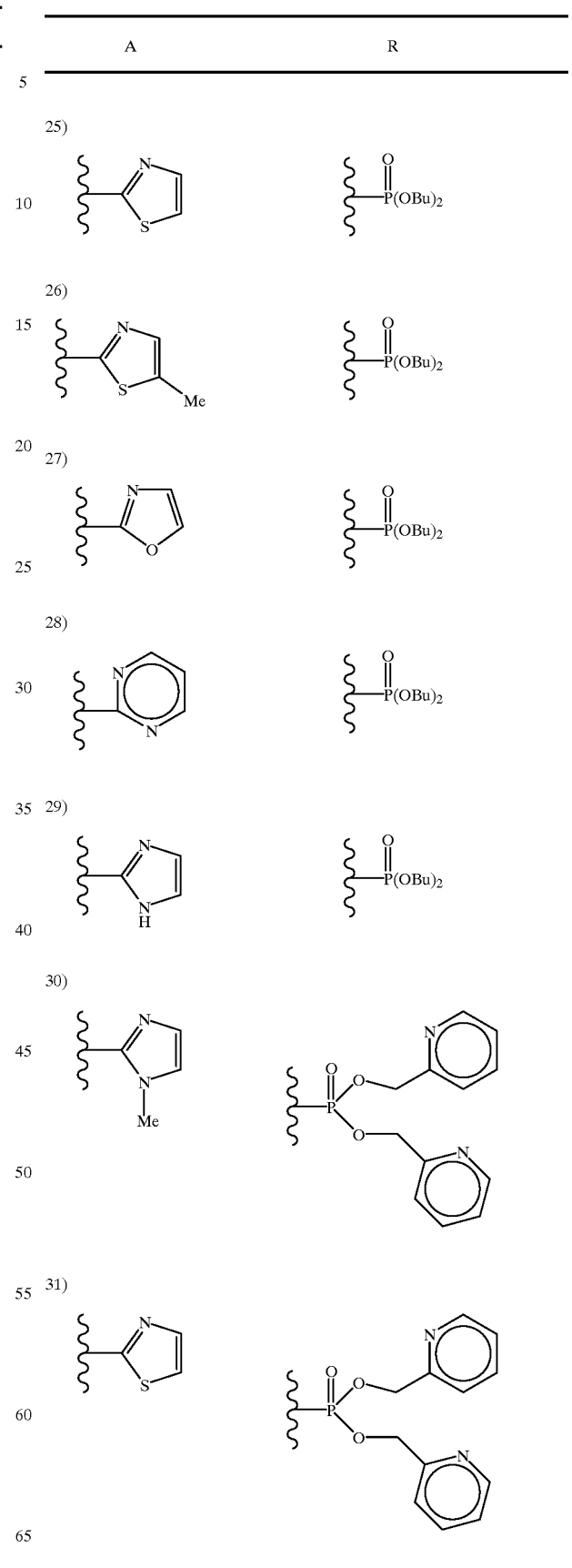 | |
| 26) | |
| 27) | |
| 28) | |
| 29) | |
| 30) | |
| 31) | |

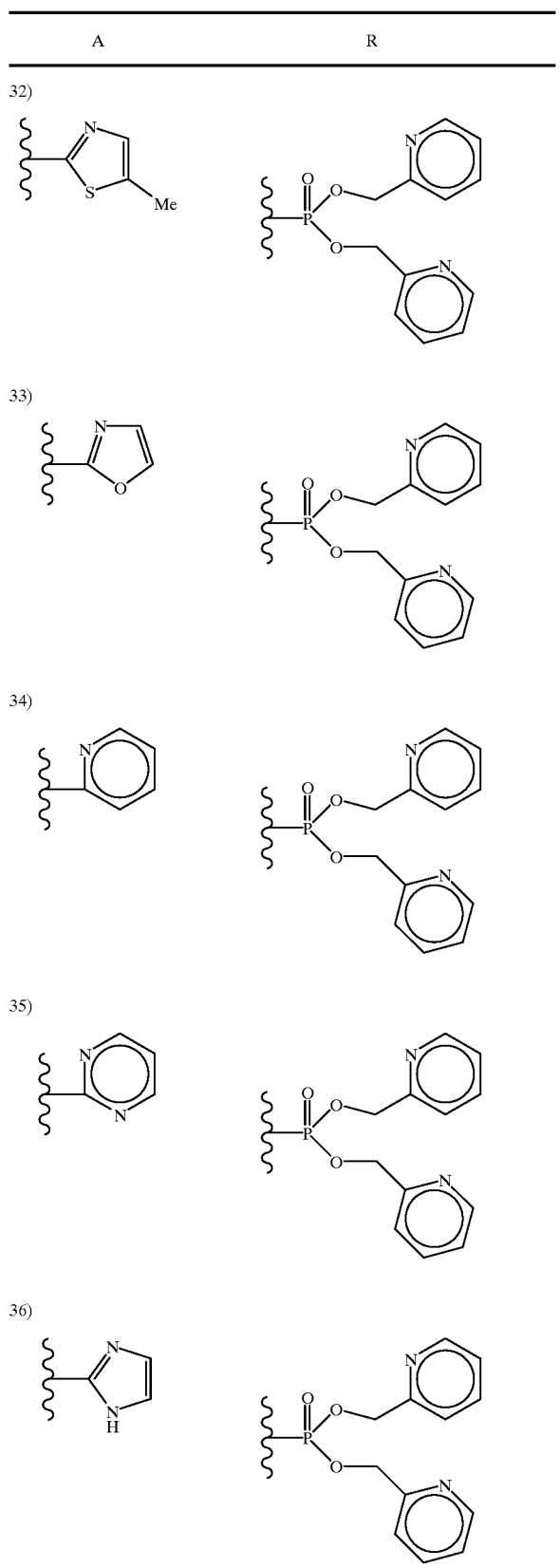
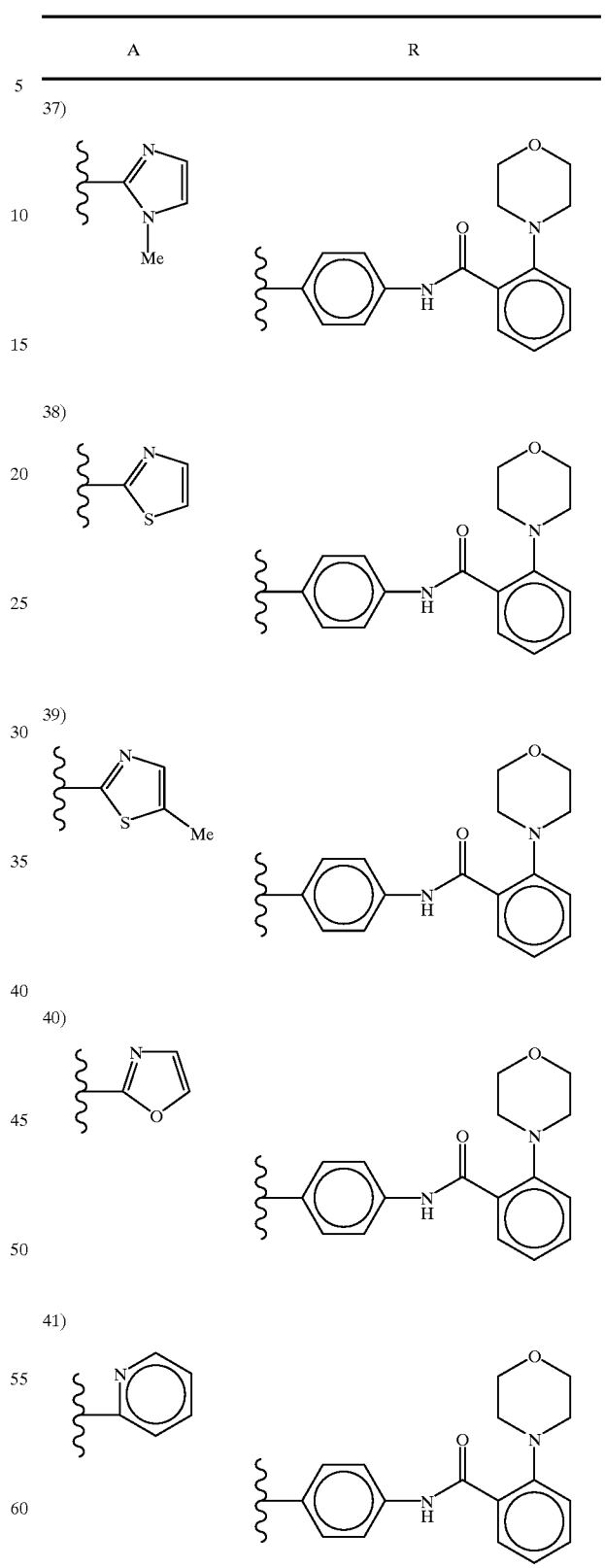

|   |   |
|---|---|
| A | R |
42) 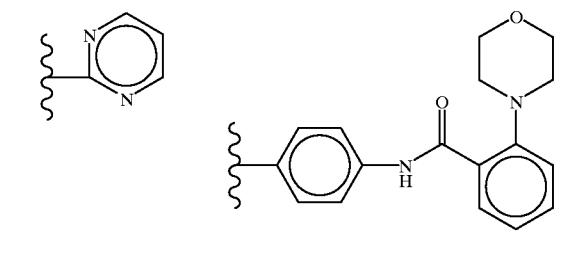
43) 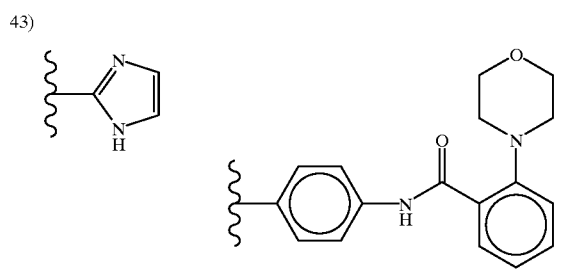
44) 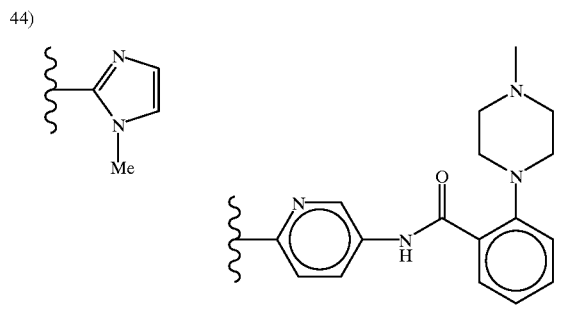
45) 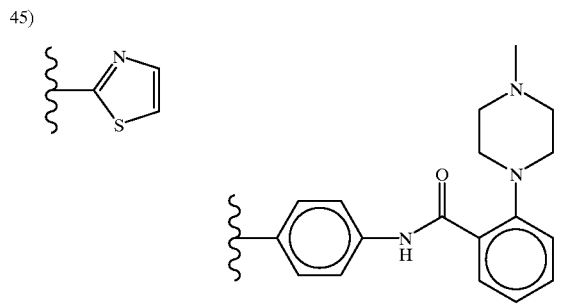
46) 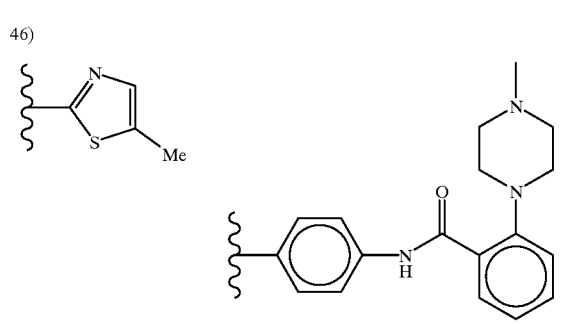
|   |   |
|---|---|
| A | R |
47) 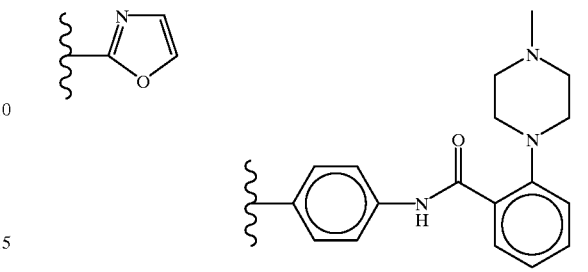
48) 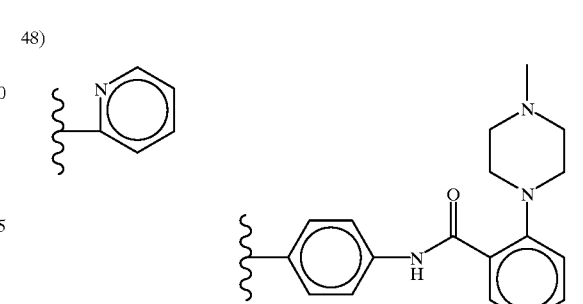
49) 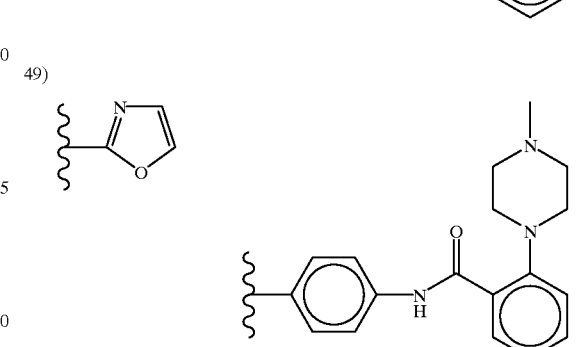
50) 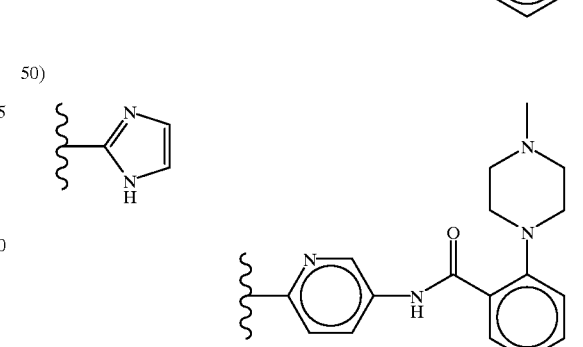
51) 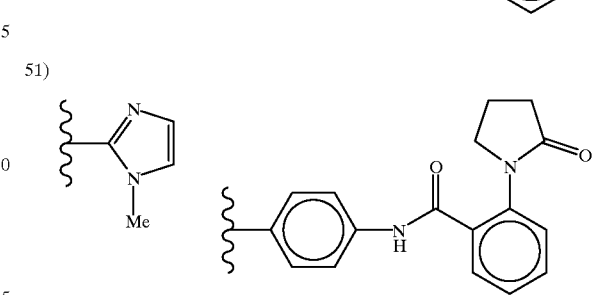

-continued
| A | R |
|---|---|
52) 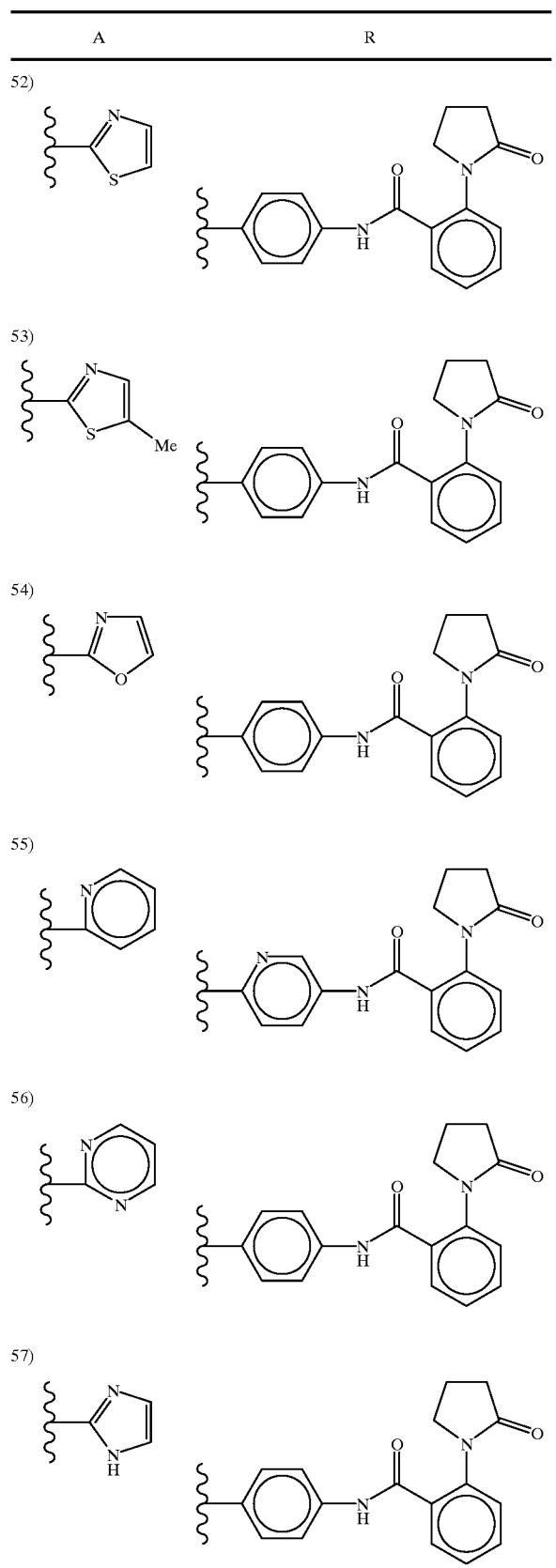
53)
54)
55)
56)
57)
-continued
| A | R |
|---|---|
58) 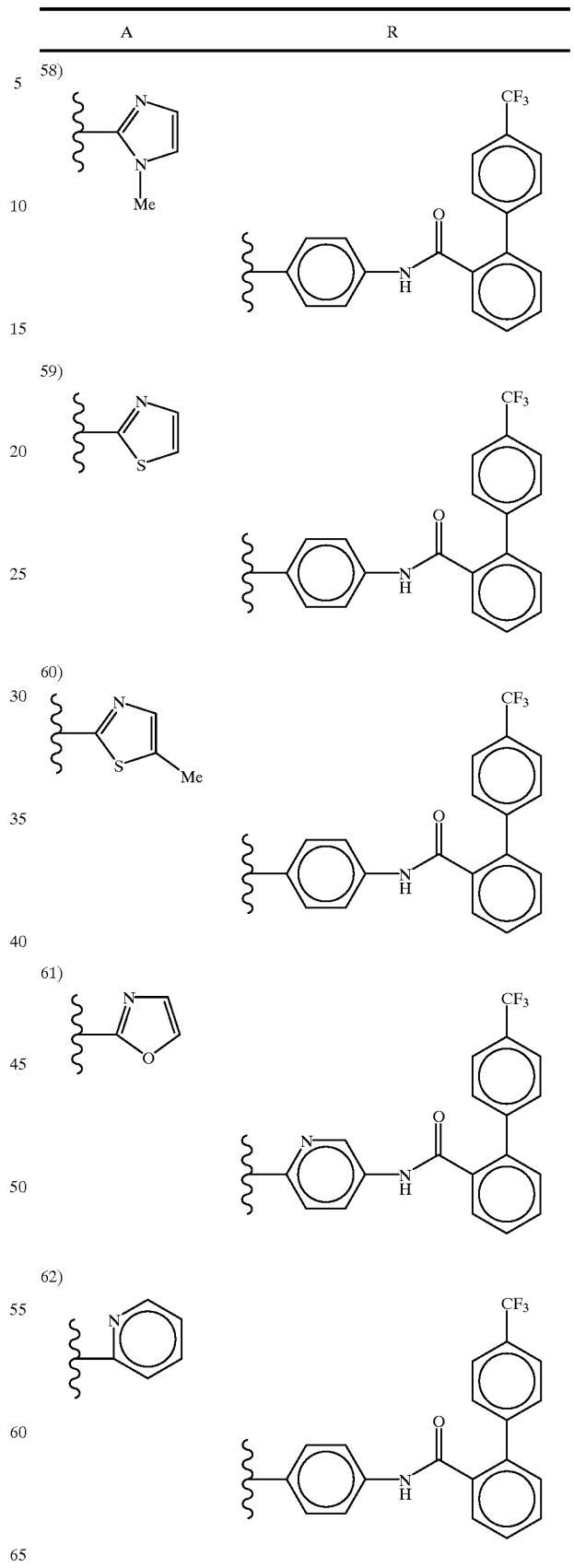
59)
60)
61)
62)

| | 69 -continued | | 70 -continued |
|---|---|---|---|
| A | R | A | R |
| 63) 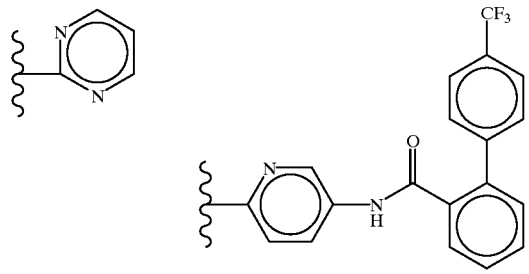 | | 68) 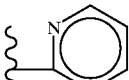 | 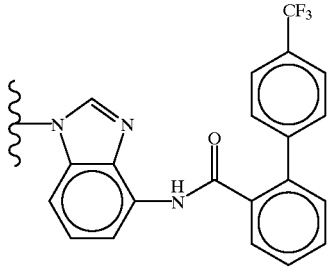 |
| 64) 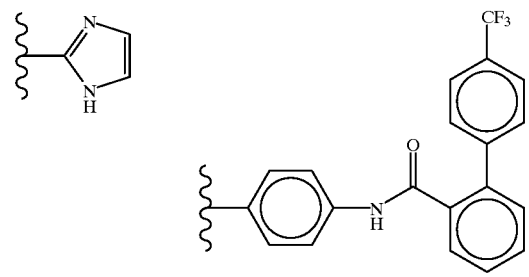 | | 69) 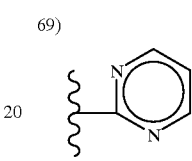 | 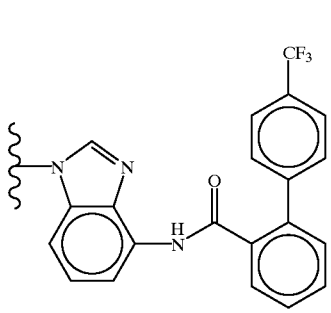 |
| 65) 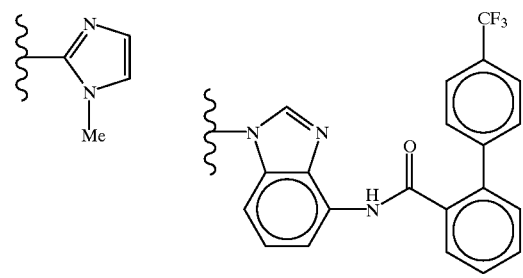 | | 70) 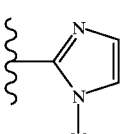 | 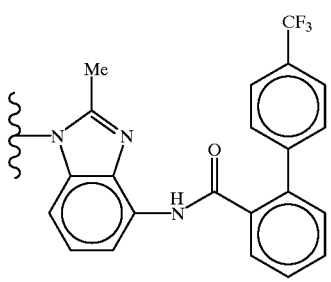 |
| 66) 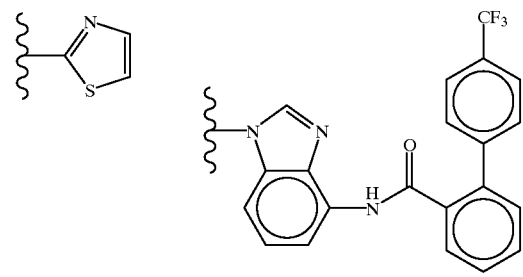 | | 71) 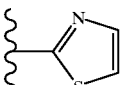 | 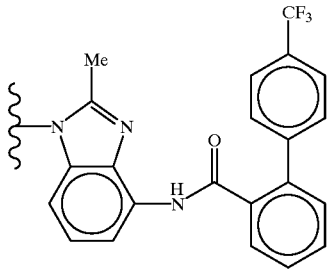 |
| 67) 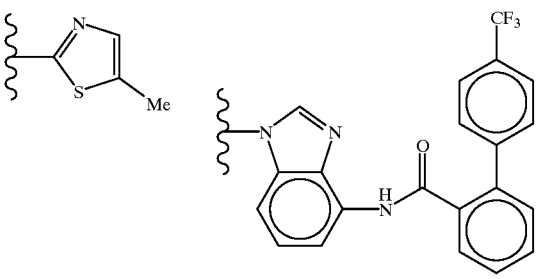 | | 72) 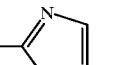 | 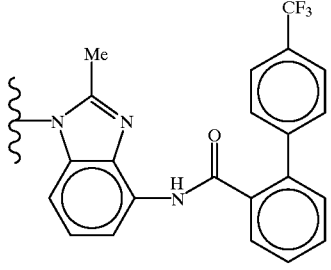 |

| A | R |
|---|---|
| 73) ![pyridine] | ![benzimidazole-Me with CF3-biphenyl amide] |
| 74) ![pyridine isomer] | ![benzimidazole-Me with CF3-biphenyl amide] |

What is claimed is:

1. A compound which has the structure

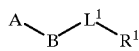

including a pharmaceutically acceptable salt thereof, or an N-oxide thereof, wherein A is

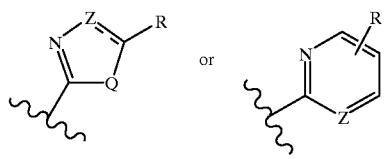

where Z is N or CH, or where Z is

or $CH_2$ when --- is a single bond;

Q is (1) —O—;
(2) —S—; or
(3)

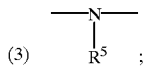

where $R^5$ and $R^{5a}$ are the same or different and are H, lower alkyl, aryl, heteroaryl or cycloalkyl;

R is H, alkyl, alkoxy, alkenyl, alkynyl, aryl, halo, heteroaryl, cycloheteroalkyl, heteroarylalkyl, cycloalkyl or cycloalkenyl, with the proviso that R cannot be alkoxy or halo when --- is a single bond;

B is a fluorenyl-type group of the structure

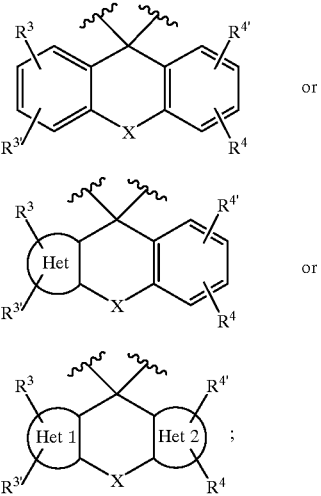

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, hydroxy, amino, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, cycloheteroalkyl, cycloheteroalkylalkyl, —PO($R^{13}$)($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); carbonylamino or aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring connected to $L^1$ at the 2, 4, 5 or 6-position; the $R^1$ group may optionally be substituted with 1, 2, 3 or 4 substituents, which can be any of the $R^3$ or $R^1$ groups or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), heterocyclyl-carbonylamino (where the heterocycle is connected to the carbonyl group via a nitrogen or carbon atom), alkylsulfonylamino, arylsulfonylamino, heteroarylsulfonylamino,

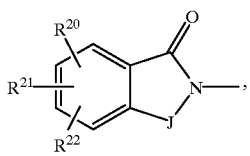

where J is: $CHR^{23}$,

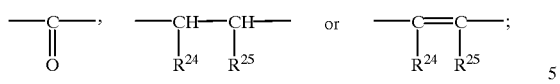

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to $R^1$, or attached via an alkylene at an open position;

$L^1$ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

$R^3$, $R^{3'}$, $R^4$ and $R^{4'}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups;

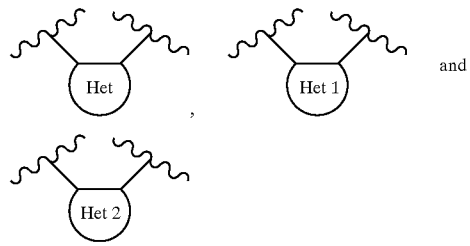

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

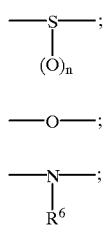

-continued

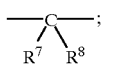  (4)

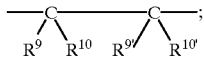  (5)

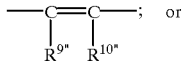  (6)

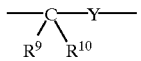  (7)

wherein

Y is O, N—$R^6$ or S;

n is 0, 1 or 2;

$R^6$ is H, lower alkyl, aryl, —C(O)—$R^{11}$ or —C(O)—O—$R^{11}$;

$R^7$ and $R^8$ are the same or different and are independently H, alkyl, aryl, halogen, —O—$R^{12}$, or $R^7$ and $R^8$ together can be oxygen to form a ketone;

$R^9$, $R^{10}$, $R^{9'}$ and $R^{10'}$ are the same or different and are independently H, lower alkyl, aryl or —O—$R^{11}$;

$R^{9''}$ and $R^{10''}$ are the same or different and are independently H, lower alkyl, aryl, halogen or —O—$R^{11}$;

$R^{11}$ is alky or aryl;

$R^{12}$ is H, alkyl or aryl;

with the proviso that where A is

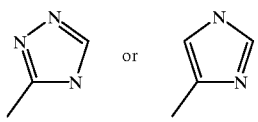

or

then $R^1$ is other than alkoxy containing 1 to 3 carbons.

2. The compound as defined in claim 1 having the structure.

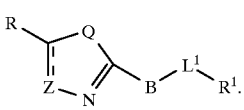

3. The compound as defined in claim 1 having the structure

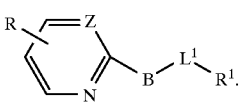

4. The compound as defined in claim 1 wherein A has the structure

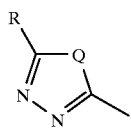

where Q is S or

5. The compound as defined in claim 1 wherein A has the structure

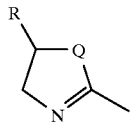

where Q is S or

6. The compound as defined in claim 1 wherein A has the structure

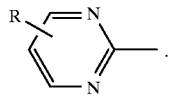

7. The compound as defined in claim 1 wherein A has the structure

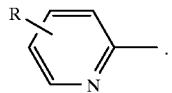

8. The compound as defined in claim 1 wherein B is

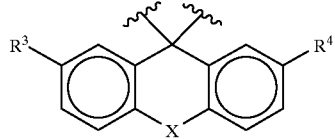

X is a bond, oxygen or sulfur;
$R^3$ and $R^4$ are the same or different and are H or F;
$R^1$ is aryl, phenyl, heteroaryl, imidazolyl, cycloheteroalkyl, pyridyl, cyclohexyl, $PO(R^{13})(R^{14})$, heteroarylthio, benzthiazole-2-thio, benzimidazoyl, indolyl, imidazole-2-thio, alkyl, alkenyl or 1,3-dioxan-2-yl, wherein each of the above is optionally substituted;
$L^1$ is a chain containing 1 to 5 atoms in a linear chain; and A is

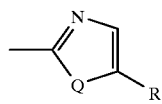

where Q is S or N-alkyl and R is H or alkyl.

9. The compound as defined in claim 8 wherein $L^1 R^1$ is

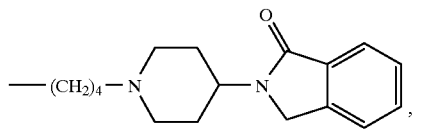

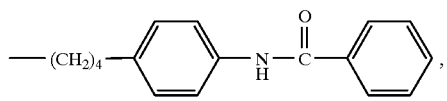

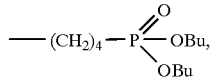

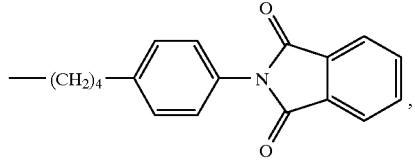

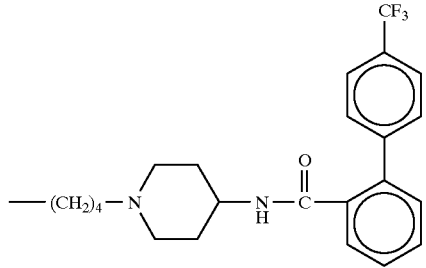

or

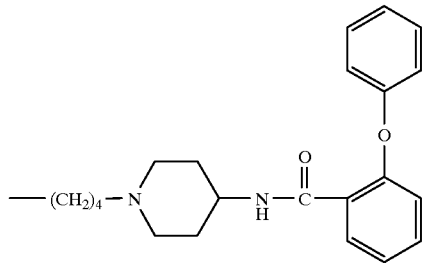

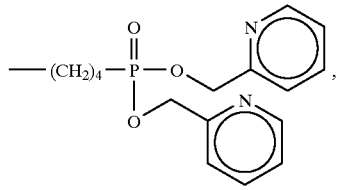

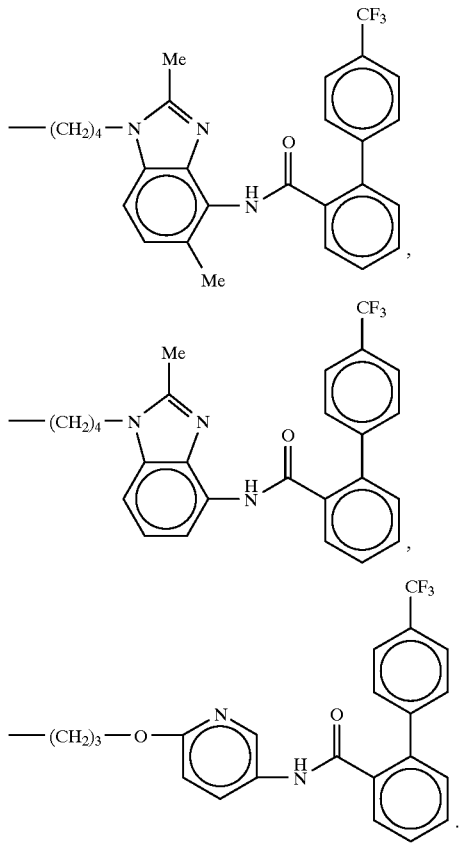

10. The compound as defined in claim 1 which is 2,3-Dihydro-2-[1-[4-[9-(5-methyl-2-thiazolyl)-9H-fluoren-9-yl]butyl]-4-piperidinyl]-1H-isoindol-1-one

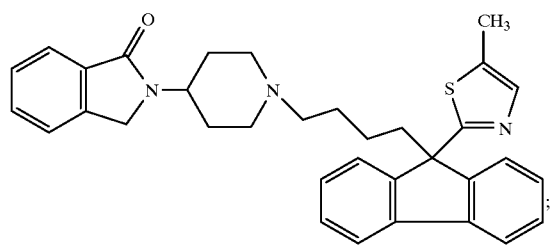

[4-[9-(1-Methyl-1H-imidazol-2-yl)9H-fluoren-9-yl]-butyl] phosphonic acid, dibutyl ester

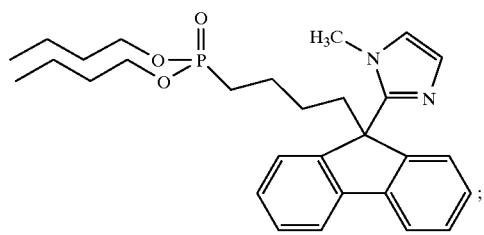

N-[4-[4-[9-(1-Methyl-1H-imidazol-2-yl)-9H-fluoren-9-yl]butyl]phenyl]benzamide

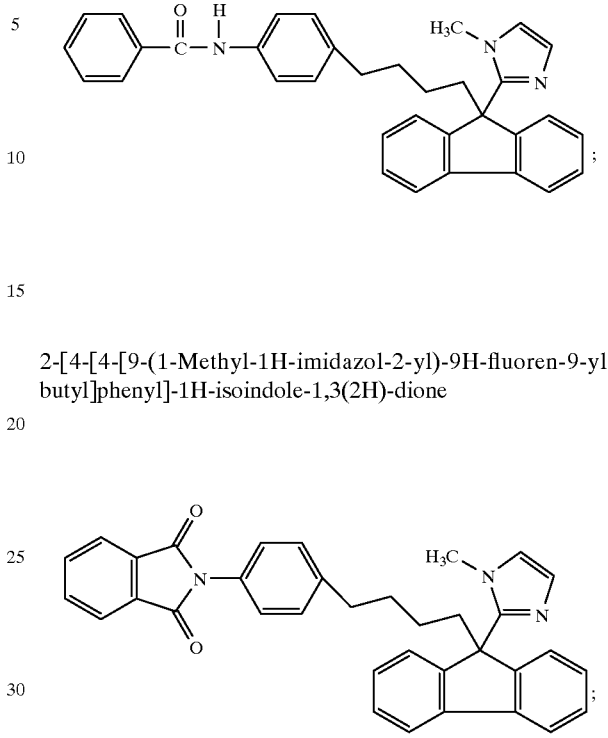

2-[4-[4-[9-(1-Methyl-1H-imidazol-2-yl)-9H-fluoren-9-yl]butyl]phenyl]-1H-isoindole-1,3(2H)-dione N-[1-[4-[9-(5-Ethyl-1-methyl-1H-imidazol-2-yl)-9H-fluoren-9-yl]butyl]-4-piperidinyl]benzamide

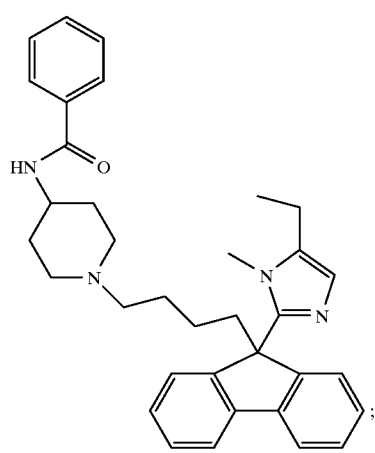

N-[1-[4-[9-(5-Ethyl-1-methyl-1H-imidazol-2-yl)-9H-fluoren-9-yl]butyl]-4-piperidinyl-2-phenoxybenzamide

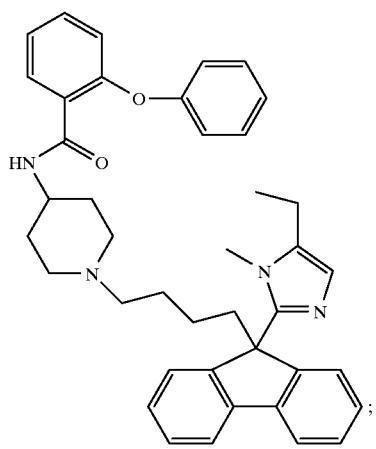

N-[1-[4-[9-(1-Ethyl-1H-imidazol-2-yl)-9H-fluoren-9-yl]butyl]-4-piperidinyl]-2-phenoxybenzamide

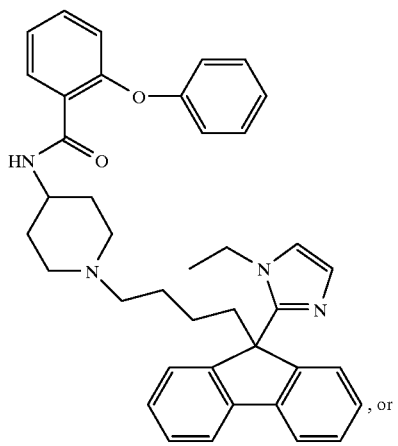

[3-[9-(2-Pyridinyl)-9H-fluoren-9-yl]propyl]phosphonic acid, dibutyl ester

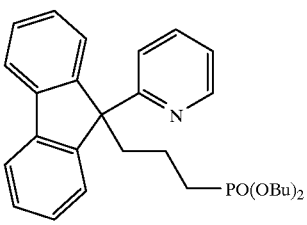

N-[1-[4-[9-(1-Ethyl-1H-imidazol-2-yl)-9H-fluoren-9-yl]butyl]-4-piperidinyl]-2-phenoxybenzamide

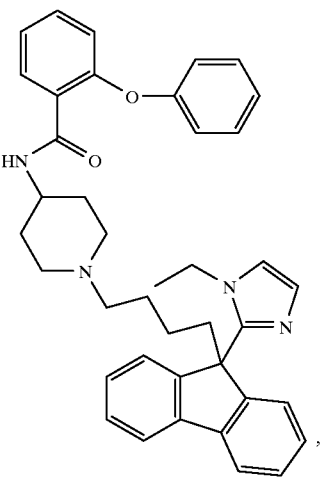

including pharmaceutically acceptable salts thereof.

11. A method for inhibiting or treating atherosclerosis, pancreatitis, type 2 diabetes or obesity in a mammalian species, which comprises administering to a patient in need of treatment a therapeutically effective amount of a compound as defined in claim 1.

12. A method of lowering serum lipid levels, cholesterol and/or triglycerides, or inhibiting and/or treating hyperlipemia, hyperlipidemia, hyperlipoproteinemia, hypercholesterolemia, hypertriglyceridemia, hyperglycemia, and inhibiting or treating atherosclerosis, pancreatitis, Type 2 diabetes or obesity in a mammalian species, which comprises administering to a patient in need of treatment a therapeutically effective amount of a compound as defined in claim 1.

* * * * *

UNITED STATES PATENT AND TRADEMARK OFFICE
CERTIFICATE OF CORRECTION

PATENT NO. : 5,965,577
DATED     : October 12, 1999
INVENTOR(S) : Joseph A. Tino It is certified that error appears in the above-identified patent and that said Letters Patent is hereby corrected as shown below:

In Claim 9, please insert following structure between lines 30 and 35.

Signed and Sealed this

Twentieth Day of June, 2000

Attest:

Q. TODD DICKINSON

Attesting Officer    Director of Patents and Trademarks